(12) United States Patent
Farahi et al.

(10) Patent No.: US 10,203,195 B2
(45) Date of Patent: Feb. 12, 2019

(54) NOISE REDUCTION TECHNIQUES, FRACTIONAL BI-SPECTRUM AND FRACTIONAL CROSS-CORRELATION, AND APPLICATIONS

(71) Applicants: Faramarz Farahi, Charlotte, NC (US); Gelareh Babaie, Charlotte, NC (US); Mehrdad Abolbashari, Charlotte, NC (US)

(72) Inventors: Faramarz Farahi, Charlotte, NC (US); Gelareh Babaie, Charlotte, NC (US); Mehrdad Abolbashari, Charlotte, NC (US)

(73) Assignee: UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 8 days.

(21) Appl. No.: 15/703,236

(22) Filed: Sep. 13, 2017

(65) Prior Publication Data

US 2018/0128591 A1 May 10, 2018

Related U.S. Application Data

(63) Continuation of application No. 14/332,948, filed on Jul. 16, 2014, now abandoned.

(51) Int. Cl.
| | |
|---|---|
| *G05B 1/06* | (2006.01) |
| *G01B 11/02* | (2006.01) |
| *G01B 11/28* | (2006.01) |
| *G01B 9/02* | (2006.01) |
| *G01B 11/06* | (2006.01) |
| *G01B 11/24* | (2006.01) |
| *A61B 3/10* | (2006.01) |

(52) U.S. Cl.
CPC .......... *G01B 9/02007* (2013.01); *A61B 3/101* (2013.01); *G01B 9/02021* (2013.01); *G01B 9/02032* (2013.01); *G01B 9/02082* (2013.01); *G01B 9/02084* (2013.01); *G01B 11/0633* (2013.01); *G01B 11/2441* (2013.01)

(58) Field of Classification Search
CPC .................................................. G01B 11/0633
See application file for complete search history.

(56) References Cited

U.S. PATENT DOCUMENTS

| | | | |
|---|---|---|---|
| 5,610,716 | A | 3/1997 | Sorin et al. |
| 8,151,644 | B2 | 4/2012 | Brandt et al. |
| 2002/0173084 | A1 | 11/2002 | Ohkawa |
| 2004/0070773 | A1 | 4/2004 | Hirose et al. |
| 2009/0071253 | A1 | 3/2009 | Olsen et al. |

(Continued)

*Primary Examiner* — Rebecca A Volentine
(74) *Attorney, Agent, or Firm* — Clements Bernard Walker PLLC; Christopher L. Bernard

(57) ABSTRACT

A measurement method and system include illuminating an object to be measured with light at two different wavelengths and an incident angle; capturing an image of the object; detecting a frequency of an interference pattern from the image using Fractional Bi-Spectrum Analysis; and calculating a thickness of the object based on the Fractional Bi-Spectrum Analysis. The thickness is calculated based on a relationship between the thickness and the frequency of the interference pattern. The Fractional Bi-Spectrum Analysis is performed on a linear medium with the two different wavelengths being known.

4 Claims, 33 Drawing Sheets

(56) References Cited

U.S. PATENT DOCUMENTS

| | | | |
|---|---|---|---|
| 2009/0182528 A1* | 7/2009 | De Groot | G01B 11/06 |
| | | | 702/167 |
| 2010/0271621 A1 | 10/2010 | Levy et al. | |
| 2010/0315591 A1 | 12/2010 | Gratton et al. | |
| 2011/0007329 A1 | 1/2011 | Woo et al. | |
| 2011/0210691 A1 | 9/2011 | Ziprani | |
| 2011/0299097 A1 | 12/2011 | Ohtsuka et al. | |
| 2012/0274946 A1 | 11/2012 | Golan | |
| 2013/0080378 A1 | 3/2013 | Huang et al. | |
| 2013/0109278 A1 | 5/2013 | Kimba | |
| 2013/0169958 A1 | 7/2013 | Goto et al. | |
| 2013/0334422 A1* | 12/2013 | Goto | G01B 11/0675 |
| | | | 250/341.8 |
| 2014/0174946 A1 | 6/2014 | Yamani et al. | |
| 2014/0239181 A1* | 8/2014 | Hattori | G01B 11/0625 |
| | | | 250/339.08 |
| 2015/0131090 A1 | 5/2015 | Osumi | |

* cited by examiner (a)

Sinusoidal pattern with frequency $f_1$
and its Fourier transform (b)

Sinusoidal pattern with frequency $f_2$
And its Fourier transform

Figure 3) (a) Fourier spectrum of the lower frequency pattern, (b) shifted Fourier spectrum of pattern with lower frequency, (c) reconstructed pattern by shifting the frequency $f_1$, this pattern has the same frequency as the second with frequency $f_2$ Figure 4) (a) Sinusoidal pattern with higher frequency; (b) reconstructed pattern from the sinusoidal pattern with lower frequency; and (c) the cross correlation of the two images

NOISE REDUCTION TECHNIQUES, FRACTIONAL BI-SPECTRUM AND FRACTIONAL CROSS-CORRELATION, AND APPLICATIONS

CROSS-REFERENCE TO RELATED APPLICATION

The present patent application/patent is a continuation of co-pending U.S. patent application Ser. No. 14/332,948, filed on Jul. 16, 2014, and entitled "NOISE REDUCTION TECHNIQUES, FRACTIONAL BI-SPECTRUM AND FRACTIONAL CROSS-CORRELATION, AND APPLICATIONS," the contents of which are incorporated in full by reference herein.

FIELD OF THE DISCLOSURE

The present invention relates to the field of noise reduction. More specifically, the invention relates to noise reduction, optical measurements, and interferometry.

BACKGROUND OF THE DISCLOSURE

Laser interferometry has tremendous applications in several fields including manufacturing and biology. One of the serious limitations of this technique is the inherent speckle noise in laser interferometry of rough surfaces. Waves reflected or transmitted by rough surfaces result in unclear interference pattern. Therefore speckle noise reduction is an important step in laser interferometry of the rough surfaces. Many methods have been proposed over the years to compensate the speckle noise in laser interferometric based technologies such as optical coherent tomography, synthetic aperture radar (SAR), ultrasound, etc. One proposed technique to suppress the speckle noise is moving the aperture of the camera. This technique averages the speckle pattern and reduces the effect of noise. The mechanism of moving the aperture increases the complexity of the system which limits the development of this technique. The post-processing methods such as median filter, Wiener filter; enhanced Lee filter, anisotropic diffusion method, etc. have more flexibility and are growing rapidly. These methods improve the signal to noise ratio, but cause the loss of details because of blurring. Fast Fourier Transform (FFT) pass band filters and power spectrum density (PSD) are alternative noise reduction techniques, which can filter off certain level of noise, although they can also distort the fringe pattern. Statistical analysis such as auto-correlation, cross correlation, and Bi-Spectrum are also used to effectively suppress the noise in optical imaging. These techniques are applied in biology, astronomy, under water imaging, and etc., where the noise level is high.

Bi-spectrum is a noise reduction technique in the analysis of nonlinear systems. It is mathematically defined as the Fourier transform of the third order cumulant of a signal:

$$B(f_1, f_2) = \lim \frac{1}{T} <X(f_1) \times X(f_2) \times X^*(f_1 + f_2)> T \to \infty$$

where, X is the Fourier transform of a random process x(t) over a finite time interval T.

Bi-spectrum is a higher-order spectrum and provides supplementary information to the power spectrum. This statistic shows the correlation between the spectral components of the system. One particular property of bi-spectrum is that it retains the phase and the magnitude information of the signal while eliminating the additive Gaussian noise. Bi-spectrum has so many applications in optical processing, geophysics, oceanography, biomedicine, astronomy, etc.

Conventionally, there are several techniques to calculate the phase and magnitude of a signal from its computed bi-spectrum, although all of these techniques require huge amount of computation and are very time consuming. Physically, in order to have a non-zero value for the bi-spectrum, the medium needs to possess a property to produce a frequency component at $f_1+f_2$, therefore for linear medium this techniques is not applicable and bi-spectrum does not contain any useful information of the signal. It would be advantageous to determine mechanisms to allow bi-spectrum techniques to apply to linear mediums.

BRIEF SUMMARY OF THE DISCLOSURE

In various exemplary embodiments, a measurement method and system include illuminating an object to be measured with light at two different wavelengths and an incident angle; capturing an image of the object; detecting a frequency of an interference pattern from the image using Fractional Bi-Spectrum Analysis; and calculating a thickness of the object based on the Fractional Bi-Spectrum Analysis. The thickness is calculated based on a relationship between the thickness and the frequency of the interference pattern. The Fractional Bi-Spectrum Analysis is performed on a linear medium with the two different wavelengths being known.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

Figure 1:
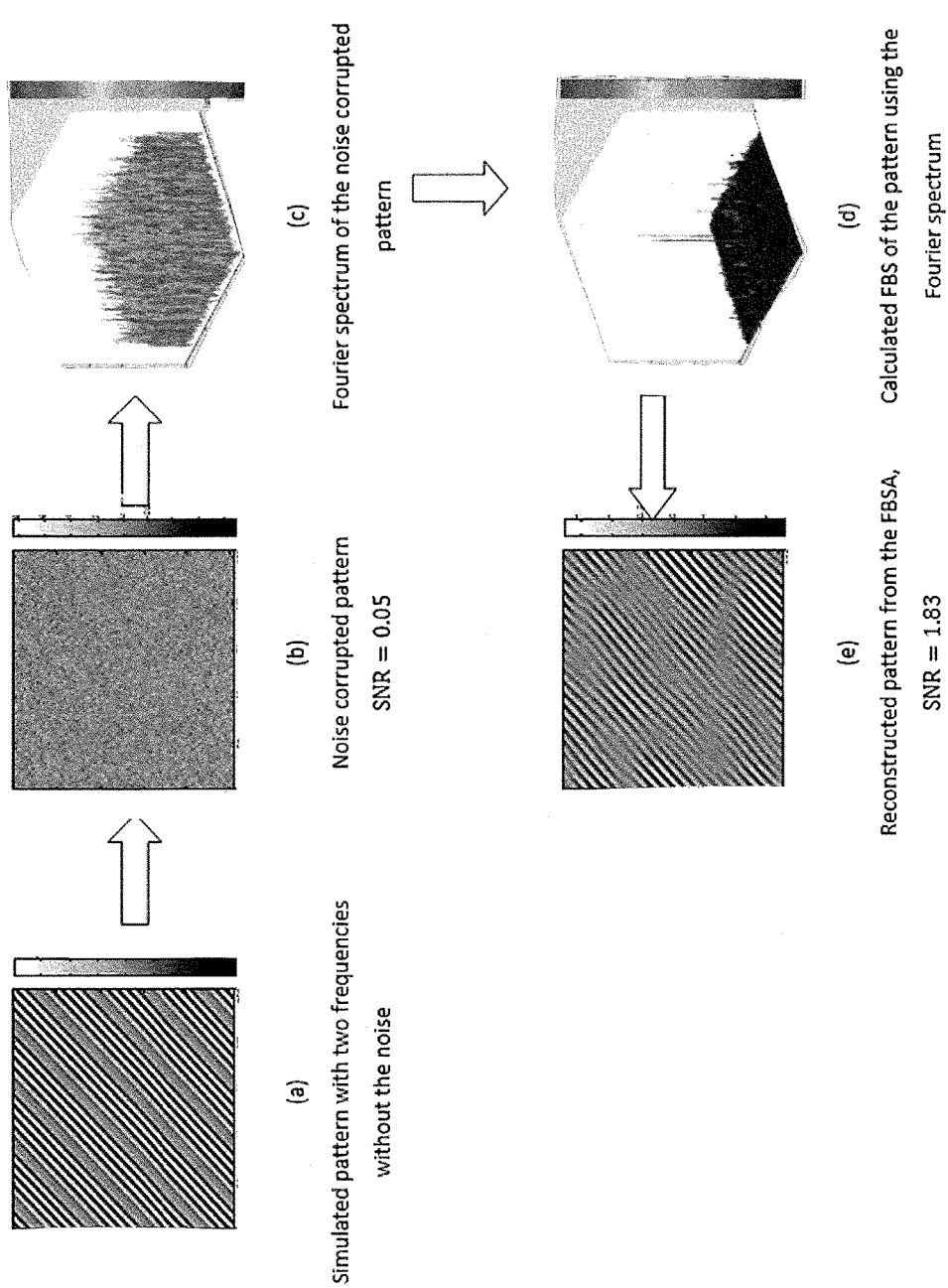
FIG. 1 illustrates a fractional bi-spectrum analysis (FBS) method configuration example.

In various exemplary embodiments, we have developed a novel technique, Fractional Bi-Spectrum Analysis (FBSA), which enables us to apply the concept of bi-spectrum on a linear medium by introducing two known wavelengths to a system. FBSA reduces the noise of the system and recovers the amplitude and phase of the signal. Variously, Fractional bi-spectrum analysis (FBSA) and Fractional cross correlation (FCC) are proposed to enhance signal information in a situation where the signal to noise ratio (SNR) is low. Mathematical models to calculate the fractional bi-spectrum, FBS, and fractional cross correlation, FCC, of an interferometric signal are proposed and verified by both simulation and experiment. FBSA can reconstruct the signal with improved signal to noise ratio. This is supported by simulation and experimental results. FBSA and FCC techniques are compared with themselves and other noise reduction techniques, such as low pass Fast Fourier Transform (FFT) and auto-correlation at different noise level. In an exemplary application, we applied the FBSA technique in order to measure the film thickness with either rough surfaces or contaminated surfaces. The results of experiments on three different samples indicate that this technique is a powerful tool to enhance the signal to noise ratio and consequently calculate the thickness of the film in the situation where the noise level is high. In another exemplary application of this technique, we applied the FBSA concept on a Michelson interferometer in order to measure the topography of rough and contaminated surfaces.

Fractional Bi-Spectrum (FBS)

Fractional bi-spectrum, FBS, is the expectation value of the product of three Fourier components in the Fourier domain of a signal. Conceptually FBSA is a mathematical function which shows the degree of dependency between the frequency components of a signal in the Fourier domain. It is defined as:

$$BS^F(v,\eta) = F(v) \times \mathcal{F}(\eta) \times \mathcal{F}^*(v+k\eta) \tag{1}$$

where, "$\mathcal{F}(v)$ and $\mathcal{F}(\eta)$" are the component of the Fourier transform of the signal at frequency v and η and k is the FBS constant.

The FBS of an interference pattern created by a single wavelength source, Eq 2, can be calculated by scanning the frequencies over the entire domain of the Fourier spectrum of the signal, Eq 3, and for each pair of frequencies substitute the amplitudes in Eq 1. As the result, the FBS of a one dimensional signal is a two dimensional matrix and the FBS of a two-dimensional pattern is a four-dimensional tensor.

$$I_a(x,y)=\alpha \cos(a_x x+a_y y) \quad (2)$$

$$\mathcal{F}_a(\omega_x,\omega_y)=\gamma\{\delta(\omega_x-a_x,\omega_y-a_y)+\delta(\omega_x+a_x,\omega_y+a_y)\} \quad (3)$$

$I_{\lambda_1}(x, y)$ is the interference pattern created by a single laser source. $\alpha$ is the background irradiance and $a_x$ and $a_y$ are the frequencies of the interference pattern in x and y direction. $\mathcal{F}(\omega_x, \omega_y)$ is the Fourier transform of the pattern, and $\delta$ is the delta function. Therefore since in the Fourier transform of a noise free interference pattern only two non-zero components at $(a_x, a_y)$ and $(-a_x, -a_y)$ exist, its FBS is always zero, since the third term of the FBS on the right side of equation 1 equals zero.

In order to have a non-zero value for fractional bi-spectrum at least two frequency components in the signal are needed, which can be created by having two laser sources with different wavelengths such as $\lambda_1$ and $\lambda_2$, Eq. 4.

$$I_{a,b}(x,y)=\alpha\cos(a_x x+a_y y)+\beta\cos(b_x x+b_y y) \quad (4)$$

$$\mathcal{F}_{\lambda_1\lambda_2}(\omega_x,\omega_y)=\gamma\{\delta(\omega_x-a_x,\omega_y-a_y)+\delta(\omega_x+a_x,\omega_y+a_y)\}+$$
$$\rho\{\delta(\omega_x-b_x,\omega_y-b_y)+\delta(\omega_x+b_x,\omega_y+b_y)\} \quad (5)$$

As a result in the Fourier spectrum of such a pattern, four distinct sharp peaks at $(a_x, a_y)$, $(-a_x, -a_y)$, $(b_x, b_y)$ and $(-b_x, -b_y)$ exist, corresponding to two interference patterns.

Suppose $f_1$ is the frequency in the 2D domain which represent $f_1=(a_x, a_y)$ and $f_2$ is the frequency which represent $f_2=(b_x, b_y)$, and $f_1<f_2$, therefore there is always an exact and unique relation between these two frequencies as follow:

$$f_2=(1+k)f_1 \quad (6)$$

where k is the FBS constant, and can be calculated by knowing the two wavelengths of the sources used Eq. 7.

$$K = \frac{\lambda_1}{\lambda_2} - 1 \quad (7)$$

Under this condition, the FBS in Eq. 1 has a non-zero value only at $f_i=f_j=\pm f_1$, where the third frequency component, $f_i+kf_j=f_1+kf_1=\pm f_2$, has a non-zero amplitude value and the FBS becomes the product of the square of the signal's amplitude at frequency $f_1$ and the signal's amplitude at frequency $f_2$. For a noise corrupted signal, FBS always has a non-zero value, but since the noise components do not follow any specific relation such as the one that signal component follows, Eq. 6, the FBS has a much higher amplitude value at the frequency of the interference signal, $\pm f_1$, compare to the noise components.

We can also calculate the FBS in such a way to determine the higher frequency of the signal, $f_2$, by a slight change in the third term of Eq. 4 as it is shown in equation 8 below:

$$BS^F(v, \eta)_{higher} = F(v) \times \mathcal{F}(\eta) \times \mathcal{F}^*(v - k'\eta) \quad (8)$$

where, $$k' = \frac{k}{k+1} \quad (9)$$

For this case FBS has a non-zero value where, $f_i=f_j=\pm f_2$.

As briefly discussed above, the FBS of a two dimensional signal is a four dimensional tensor, $BS^F(v_1, \eta_1, v_2, \eta_2)$, where $(v_1, \eta_1)$ are representing the frequencies of one of the interference patterns and $(v_2, \eta_2)$ are representing the frequencies of the second interference pattern. Analyzing a four dimensional tensor is not an easy task, however the plane of interest, the plane where the peaks will show up, is the plane where $v_1=\eta_1$ and $v_2=\eta_2$. Therefore we only look for the $BS^F(v_1, v_1, v_2, v_2)$, which is a two dimensional matrix. In the next section the proposed mathematical concept for FBSA is simulated using a MATLAB code.

Simulation of Fractional Bi-Spectrum

A MATLAB code is generated in order to calculate the FBS of a two dimensional signal with two interference patterns, with different frequencies. A white Gaussian noise is added and its amplitude, $\gamma$, is increased in steps, Eq. 10. The FBS of the noise corrupted signal is calculated at each step in order to find the frequency of the signal component. In order to calculate the error the simulation code also contains the Monte Carlo method for hundred of iteration. After detecting the pattern frequency using FBS, a low pass filter ran through the Fourier spectrum of the pattern around the detected frequency. By applying the inverse Fourier transform on the filtered Fourier spectrum, the pattern with the lower noise level is reconstructed.

$$I(x,y)=\alpha \cos(a_x x+a_y y)+\beta \cos(b_x x+b_y y)+\gamma(\text{noise}) \quad (10)$$

In FIG. 1, the frequency with a lower value is reconstructed and shown; however we could reconstruct the upper frequency component as well. The detected frequency of the signal from FBS at each level of noise is compared with the noise free signal frequency. The results of this simulation for the detected frequency and the signal to noise ratio at different noise level is shown in table 1 below.

Fractional Cross-Correlation (FCC)

The spatial cross-correlation is a statistical tool to measure the similarity between two stationary data sets. One of the widely used applications of the cross-correlation is in the field of pattern recognition. The cross-correlation of two distinct sinusoidal patterns with variable frequencies does not contain any useful information from neither of the patterns, while the cross-correlation of two sinusoidal patterns with same frequencies, contains a sinusoidal pattern which its frequency is the same frequency of each pattern. In this work we propose a new technique, Fractional Cross Correlation (FCC), which enables us to calculate the frequency of a sinusoidal pattern by having two distinct sinusoidal patterns with different frequencies.

Fractional Cross-Correlation (FCC) Method

Figure 2:
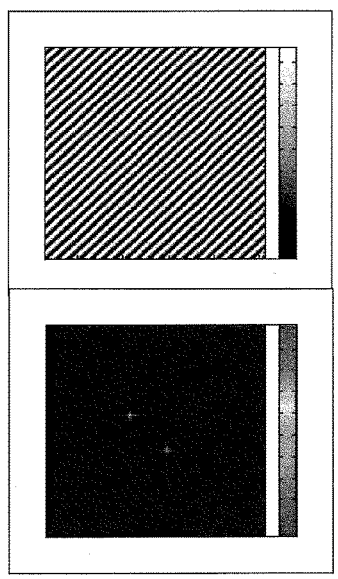
FIG. 2 illustrates a two distinct sinusoidal patterns and their Fourier spectrum.
Figure 2:
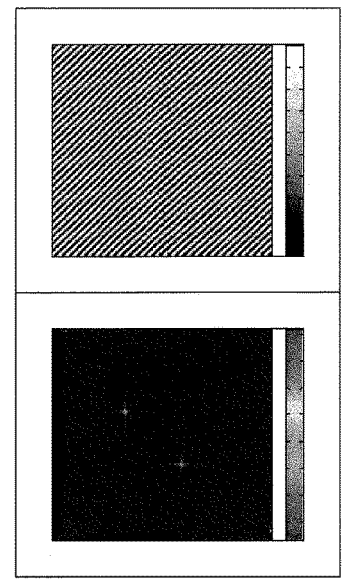

Suppose we have two sinusoidal patterns at frequency $f_1=(a_x, a_y)$ and $f_2=(b_x, b_y)$ FIG. 2, where $f_1=(1+k)f_2$. k is the FCC constant, which can be calculated by knowing the wavelengths of the sources, which create sinusoidal (interference) patterns. Therefore in the Fourier domain of each of this signals two distinct peaks exist, which represent the frequency of each pattern.

Figure 3:
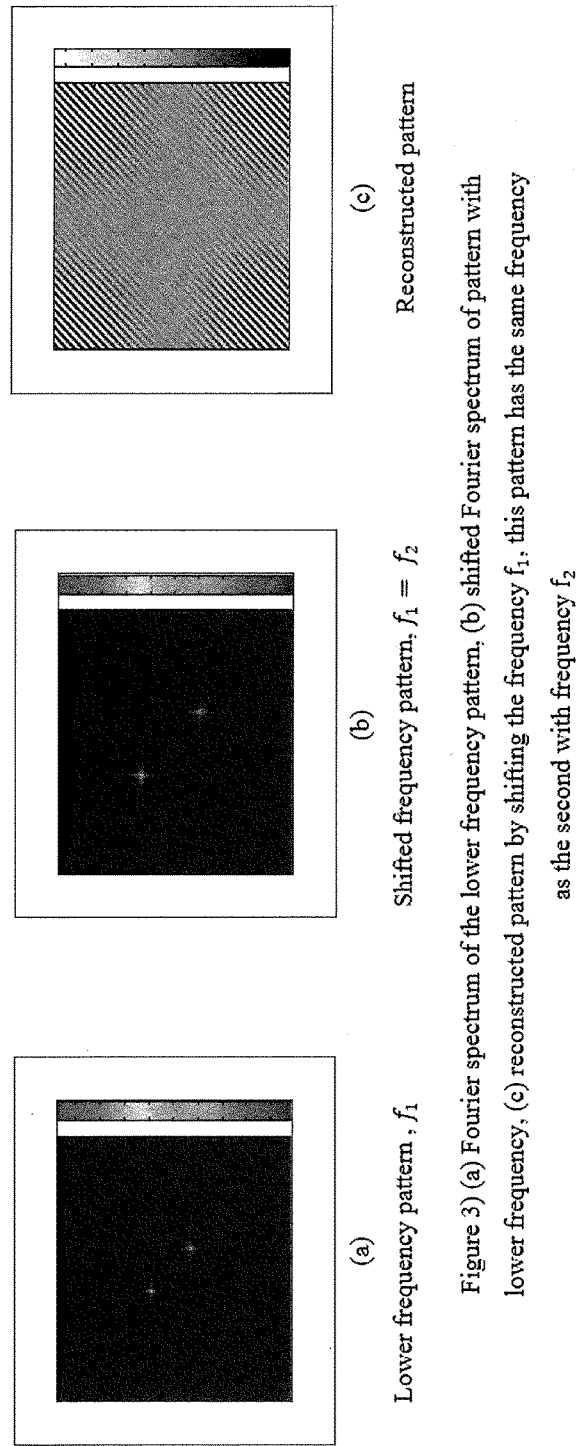
FIG. 3 illustrates (a) Fourier spectrum of the lower frequency pattern, (b) shifted Fourier spectrum of pattern with lower frequency, (c) reconstructed pattern by shifting the frequency $f_1$, this pattern has the same frequency as the second with frequency $f_2$.
Figure 4:
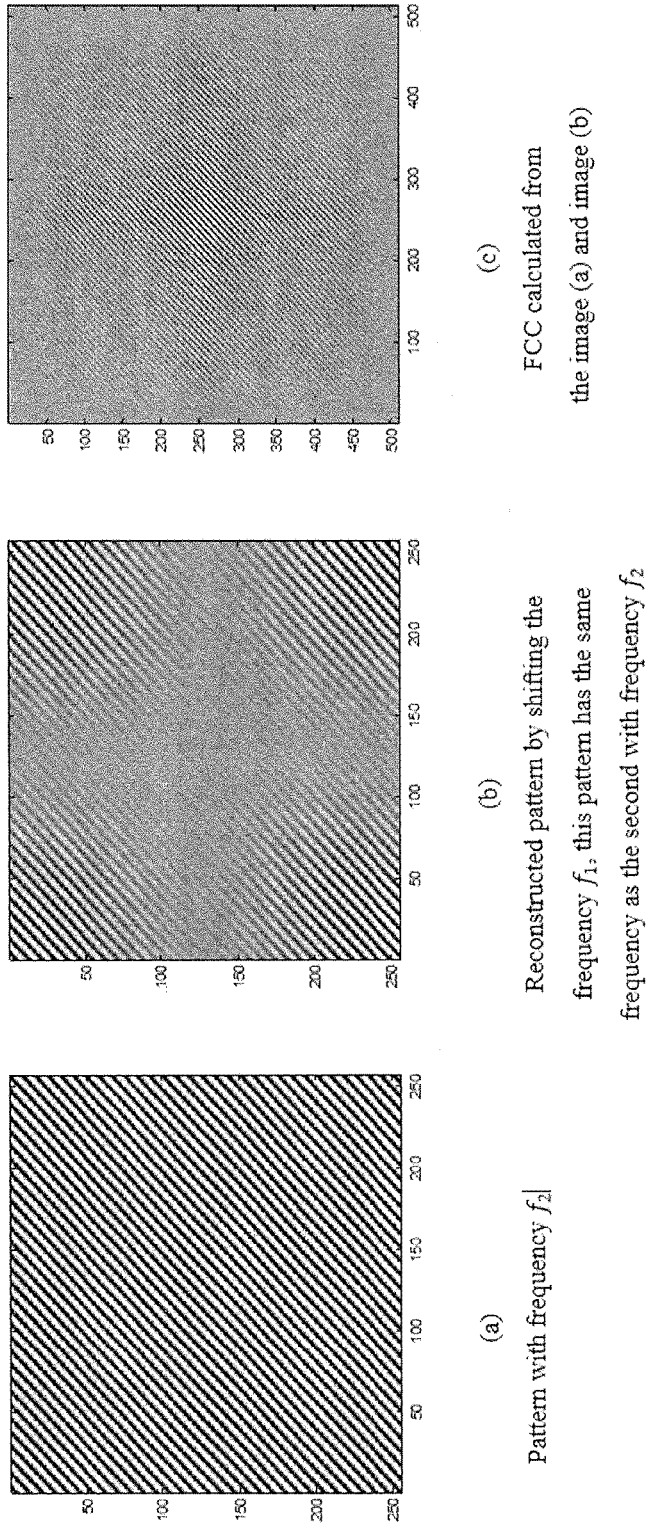
FIG. 4 illustrates (a) Sinusoidal pattern with higher frequency, (b) reconstructed pattern from the sinusoidal pattern with lower frequency, and (c) the cross correlation of the two images.

Since we know how exactly these two frequencies are related, $f_2=(1+k)f_1$, we can scale one of the frequencies in the Fourier domain, for example, $f_1$, with respect to frequency $f_2$. At this point by applying the inverse Fourier transform on the shifted frequency pattern, an interference pattern with the same frequency as the other pattern with frequency $f_2$, can be obtained (FIG. 3).

We can find the cross correlation of the new reconstructed pattern and the first initial pattern. Since these two patterns have the same frequency, their cross-correlation contains the sinusoidal pattern with the same frequency of f2. We can find this frequency by fitting the FCC pattern to a sinusoidal function.

A Comparison Between FBSA, and FCC with Other Optical Noise Reduction Technique:

For the auto-correlation analysis, the spatial auto-correlation of the pattern with the higher frequency is calculated using a MATLAB code. A Gaussian white noise is added to the pattern and increased in steps. A sinusoidal function is fitted to the calculated auto-correlation function at each level of noise, in order to find the frequency of the pattern.

For both FCC and auto-correlation techniques, we added a white Gaussian noise to all patterns and increased its amplitude step by step to analyze how well these techniques can improve the signal to noise ratio compare to the FBSA and FCC. The results for different noise level for FBSA, low pass FFT, auto-correlation and FCC are all shown in table 1, below.

TABLE 1

Comparison between FBSA, FFT: low pass Fourier transform, AC: Auto Correlation analysis and FCC: Fractional Cross-correlation analysis

| Amplitude of the noise in the image | Detected frequency | | | | Error Calculated by Monte Carlo simulation | | | | Signal to noise ratio (SNR) | |
|---|---|---|---|---|---|---|---|---|---|---|
| | FBSA | FFT | AC | FCC | FBSA | FFT | AC | FCC | FBSA | FFT |
| 0 | 20 | 20 | 20.6 | 20.52 | 0% | 0% | 0% | 0% | 3 | 1.7 |
| 5 | 20 | 20 | 20.6 | 20.54 | 0% | 3% | 2% | 0% | 3.05 | 1.6 |
| 10 | 20 | 20 | 20.6 | 20.51 | 0% | 26% | 6% | 18% | 3.01 | 1.5 |
| 12 | 20 | 20 | 20.6 | 20.5 | 7% | 42% | 84% | 12% | 2.85 | 1.45 |
| 15 | 20 | — | — | 20.45 | 9% | — | — | 36% | 2.52 | — |
| 18 | 20 | — | — | 20.36 | 10% | — | — | 54% | 2.13 | — |
| 20 | 20 | — | — | 20.35 | 20% | — | — | 83% | 1.96 | — |
| 25 | 20 | — | — | 20.3 | 58% | — | — | 92% | 1.7 | — |
| 30 | 20 | — | — | 20.5 | 85% | — | — | 95% | 1.52 | — |

From the obtained data, shown in table 1, the low pass FFT and the autocorrelation analysis cannot calculate the correct frequency component for the noise level above 12, or signal to noise ratio of $$\frac{1}{2*12^2} = 0.0035,$$

while with the FBSA and the modified cross correlation the correct frequency of the pattern up to the noise level of 30 can be obtained. By comparing the error index of FBSA and modified cross correlation, FCC, it is obvious that FBSA provides the frequency of the pattern with much higher accuracy compare to the FCC. Since in FCC technique we find the frequency by fitting a sinusoidal function into it, this technique has sub wavelength accuracy. Therefore by combining the FBSA technique with the FCC we can extract the correct frequency component with a better accuracy. The FBSA can determine the correct frequency component at high level of noise and FCC can extract the sub wavelength information of the same frequency.

Experimental Results for Film Thickness Measurement by FBSA:

Film thickness measurement has numerous applications in different fields such as engineering and biology. Many different optical and non-optical techniques have been developed to measure the film thickness. Transmission electron microscopy (TEM) and scanning electron microscopy (SEM) are two non-optical methods for film thickness measurement, which can give accurate images from the cross section of the film in order to calculate the film thickness. The result of TEM and SEM is independent of the film roughness, although in both SEM and TEM the sample needs to be placed in the vacuum chamber which might dehydrate the sample and consequently affect its thickness. SEM and TEM are suitable to measure the film with thickness of a few nanometers to less than 1 μm. These techniques are also costly and very time consuming. Step-edge techniques are alternative non-optical methods to measure film thickness. In these techniques a step edge needs to be generated on the film and the sample profile is measured across the generated edge by a stylus profiler.

This method can provide the thickness information in the air, therefore it does not dehydrate the sample but it is a destructive method. Generating the step edge on the sample itself is a very complicated process. Ellipsometry and reflectometry are two non-destructive optical techniques, which are only suitable for highly flat and specular surfaces. These techniques have low lateral resolution and can measure the film thickness range from a fraction of a nanometer to almost 5 μm in visible to near infrared wavelength range. Recently, interferometric techniques have played an important role in measuring film thickness by either looking at the spectral nonlinear phase or the Fourier amplitude of the interferometric signal. The Fourier amplitude method is a well-known non-destructive technique among the interferometric techniques, which can measure the film thickness varying from 1 nm to a few millimeters. The accuracy of thickness measurement based on Fourier amplitude is usually limited by the noise level in the system and the fringe visibility. This limits the capabilities of Fourier amplitude technique to measure the thickness of the films in the presence of impurities, non-uniformity, and roughness. For these types of films a further step is usually needed in order to reduce the noise. In this work we propose to apply FBSA as a noise reduction tool to measure the thickness of the films with rough surfaces.

Figure 5:
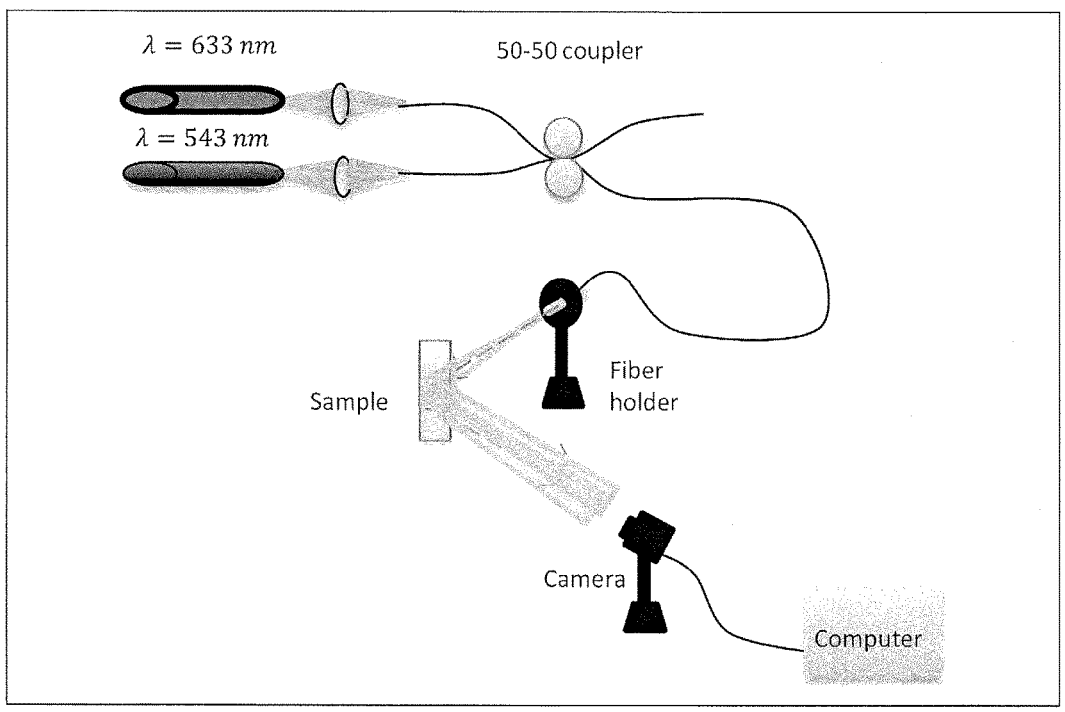
FIG. 5 illustrates a schematic of an experimental setup for FBSA with two wavelengths.

A schematic of the experimental setup for film thickness measurement using the FBSA is shown in FIG. 5. As it is illustrated two He—Ne lasers at $\lambda_1$=632.8 nm and $\lambda_2$=543 nm are coupled to single mode fibers. The output of the fibers is combined together by a fiber coupler and illuminates the film with incident angle of Θ which was 50° in our experiment. The distance between the tip of the fiber and the sample was 1 cm and the distance between the sample and camera was 2.5 cm. Finally, the image is transferred to the computer for further analysis. This system is calibrated by a glass wafer with a known thickness of 180 μm.

Figure 6:
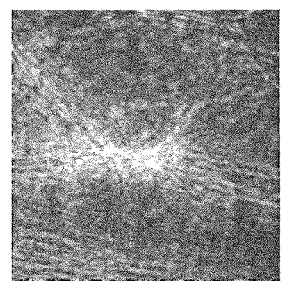
FIG. 6 illustrates (a) Captured interference image from a clear glass wafer for calibration (b) Captured interference image from an etched glass wafer, (c) Captured interference image from a double layer tape, and (d) Captured interference image from a coated layer on a solder bump sample.
Figure 6:
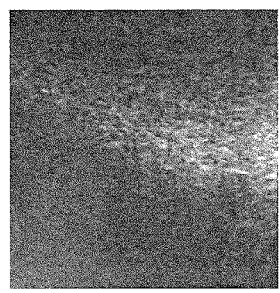
Figure 6:
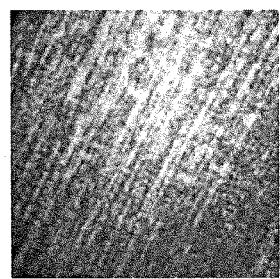
Figure 6:
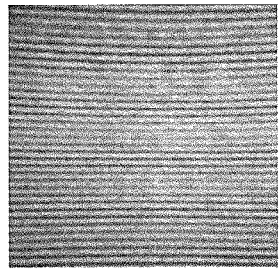

The accuracy of this system with the implemented setup is 4 µm. The captured images for samples are shown in FIG. 6.

For each sample, the frequency of the pattern is detected using the FBSA and the thickness is calculated. In order to validate our results, we have tried to measure film thicknesses with other metrology tools. We could measure the thickness of the etched glass and the tape with a digital caliper with 0.01 mm error. For the polymer coating layer on a non-uniform metal substrate, the last sample, we have tried to measure its thickness with white light interferometer, but this instrument could not measure the thickness of the film due to the low level of intensity which reflects back from the sample into the interferometer. No other optical thickness measurement device could measure this sample; therefore we used a profiler to measure the thickness of the layer around a furrow that we created on the sample. We have measured the film thickness to be 70.2 µm. Another issue with the sample is its non-uniformity. The thickness of this sample is variable on different areas on the sample due to wire pattern beneath this layer. Therefore we applied FBSA at 5 different spot on the sample. The thickness range that we found for this sample with FBSA is between 44 µm and 91 µm. Table 2 summarizes the result of the experiment for thickness measurement.

TABLE 2

Results of FBSA on three different samples and their calculated thickness

| Sample | Calculated Spatial Frequency by FBSA (m/m) | FBSA SNR | FBSA film thickness (µm) | Measured height with other technique (µm) |
|---|---|---|---|---|
| Tape | $f_x = 0$ $f_y = 6$ | 1.93 | 67.3 ± 4 | 60 ± 10 |
| Etched glass | $f_x = 0$ $f_y = 11$ | 2.5 | 102.8 ± 4 | 92 ± 10 |
| Polymer coating | $f_x = 5$ $f_y = 6$ | 1.96 | 44.2 ± 4 to 90.7 ± 4 | 70.2 |

Simulation and Experimental Results for Surface Topography Measurement by FBSA:

Topography measurement of the objects has an important role in manufacturing process. Optical techniques have played an important role in the surface metrology. Currently several different optical instruments and methods are available which can measure the topography of the object such as: optical profiler, microscope systems, Moire and structured light method, holographic method, speckle interferometry method, optical scattering, white light interferometry, confocal microscopy, etc. Among all these methods laser interferometry technique that can reveal the surface information in a single image has less merit. The main reason is the speckle noise, which is inherent in the interference of coherent lights. One of the important features in laser interferometry is the degree of smoothness of the interfering waves. Waves reflected or transmitted by rough surfaces shows rapid amplitude and phase fluctuations, which makes the interference pattern unclear and in some cases impossible to analyze for topography of the surface to be obtained. The amount of amplitude fluctuation depends on the surface roughness. When a coherent plane wave is incident on a rough surface several spherical waves reflect off the sample in all directions. These reflected waves can randomly interfere with one another and create a speckle pattern with rapid fluctuation in its intensity.

In surface topography measurement using the interferometry techniques, the speckle is an undesirable effect which corrupts the real data. Therefore a further de-noising step is needed to make the interference pattern become a useful source of information. In this work we have applied FBSA as a noise reduction technique and consequently calculated the topography of rough surfaces. We first simulated the system by defining an object with a semi spherical shape. The reflected signal from such an object contains two interference patterns at two different frequencies. The height information (topography) of the object is modulated to the phase of these patterns, Eq. 12. Speckle is a multiplicative noise, which can be converted to the additive noise by taking the logarithm of the initial signal, therefore in the simulation instead of multiplying a random noise to our signal; we just added a random Gaussian distribution noise to the logarithm of the simulated signal. The amplitude of the noise is increased in steps, and FBSA is applied to the noise corrupted signal. FBSA extract the frequency of the signal and reconstruct the phase map of the image by using a band pass filter around the detected signal calculating the inverse of Fourier transform.

$$I(x,y)=\sin(a_1x+b_1y+\varphi_1(x,y))+\sin(a_2x+b_2y+\varphi_2(x,y))+\gamma^*\text{noise} \quad (12)$$

Figure 7:
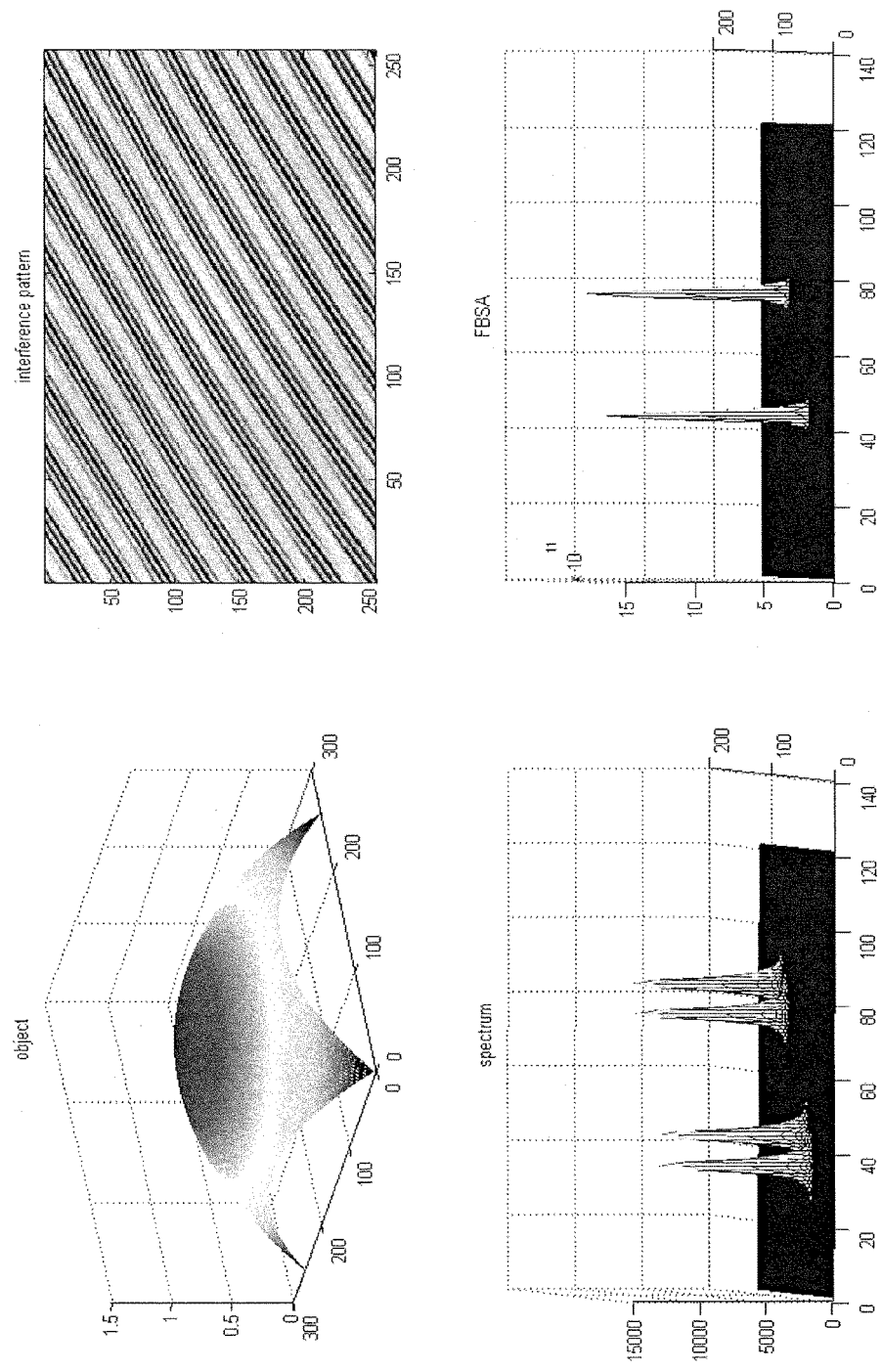
FIG. 7 illustrates a simulation for FBSA for topography measurement.
Figure 8:
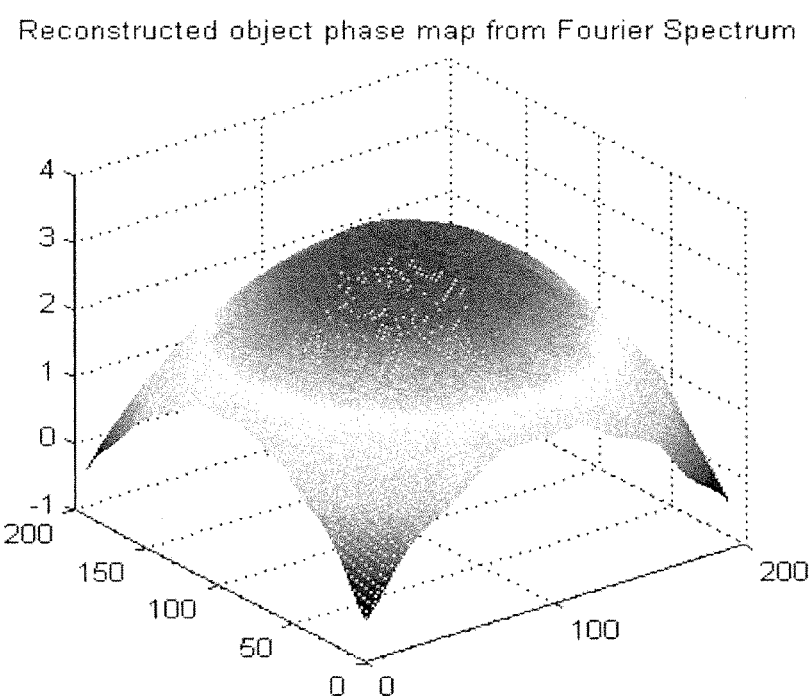
FIG. 8 illustrates a Reconstructed phase map from the FBSA of FIG. 7.
Figure 9:
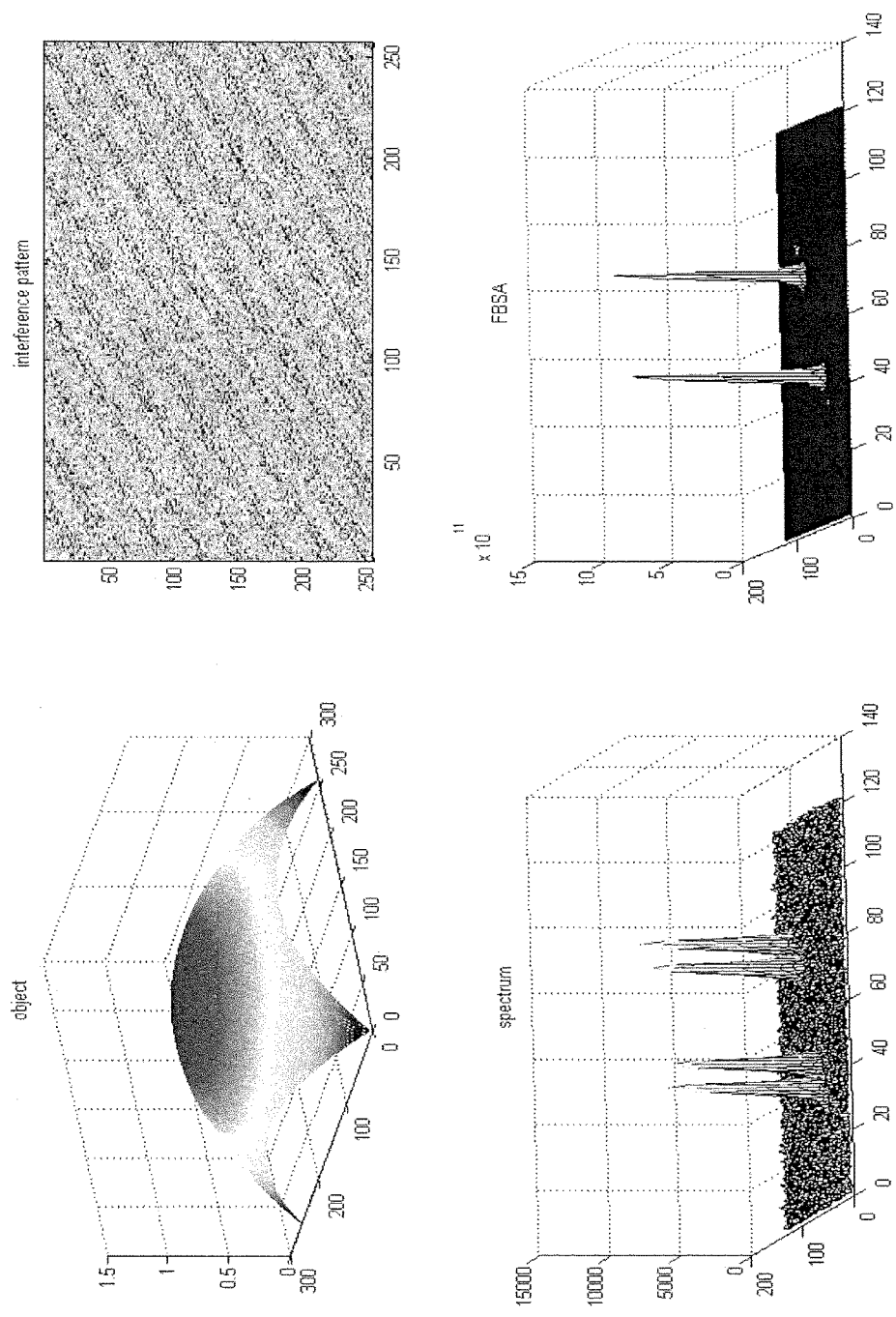
FIG. 9 illustrates a simulation for FBSA for topography measurement.
Figure 10:
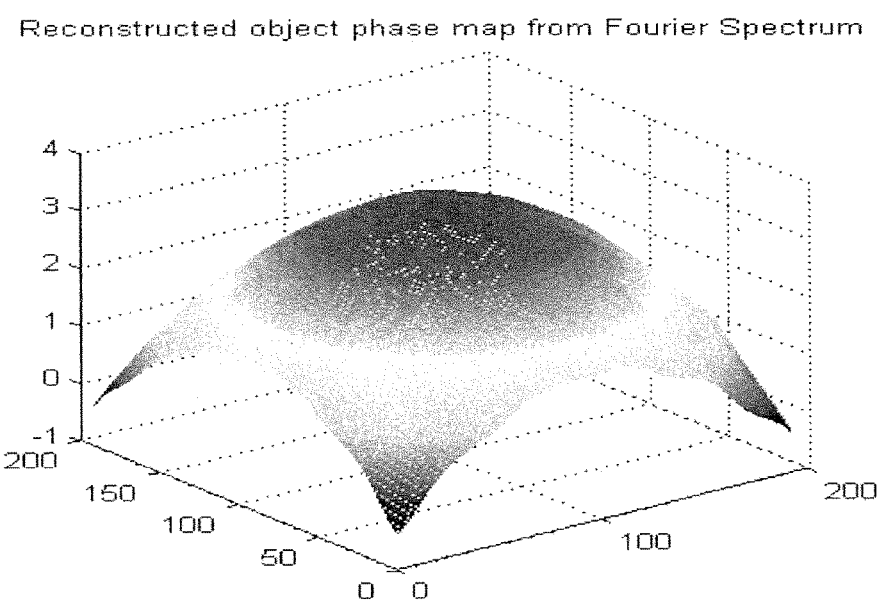
FIG. 10 illustrates a Reconstructed phase map from the FBSA of FIG. 9.

FIG. 7 shows the object of interest, the reflected pattern which contains the height information of the object, its Fourier spectrum and finally it's calculated FBS. FIG. 8 shows the reconstructed phase map of the object from the FBSA. We then increased the noise amplitude and the FBSA was calculated. The results are shown in FIGS. 9 and 10.

Experimental Results for Surface Topography Measurement by FBSA:

As discussed herein, in order to be able to apply FBSA, a source with at least two wavelengths is needed. To satisfy this condition we launched one red He—Ne laser at λ=633 nm and one green He—Ne laser at λ=543 nm to single mode fibers and combined them using a 50-50 coupler. The output of the coupler, which includes both wavelengths, is used as the input source of a Michelson interferometer. The combined beam is collimated using a 5× lens and a beam splitter guides this combined source to both arms of the interferometer. We first adjusted the interferometer by placing two clean mirrors in both arms and then contaminated one of the mirrors with a layer of oil and dust.

Figure 11:
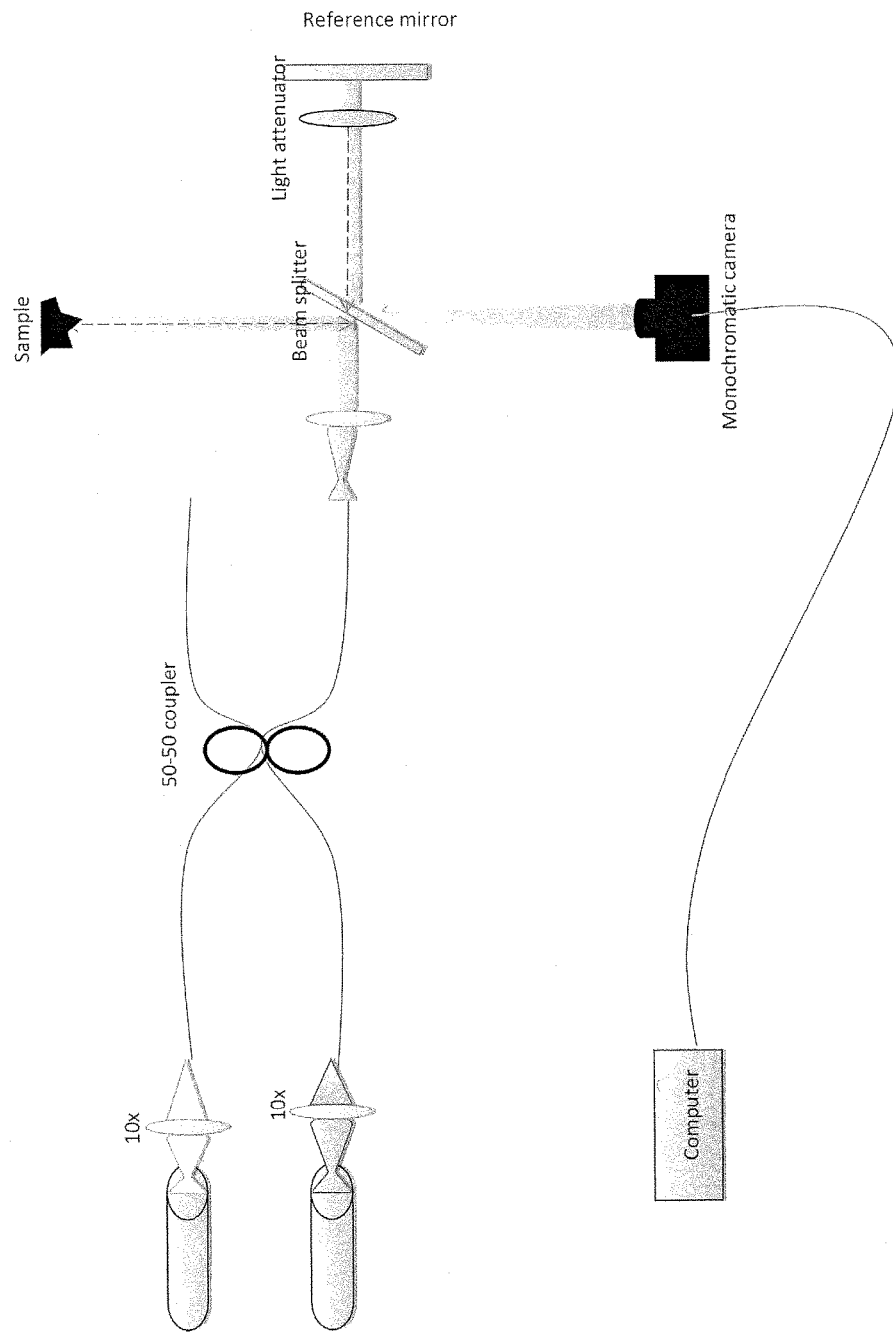
FIG. 11 illustrates a schematic of an experimental set up, two He—Ne lasers one at red wavelength (633 nm) and the other at green wavelength (543 nm)

The interference pattern of the reference beam, reflecting back from the arm, which the clean mirror is placed on it, and the speckle pattern reflecting back from the grimy mirror were captured by a monochromatic camera. The reflected light back from the arm, where the grimy mirror is placed, showed rapid fluctuation in its intensity. Therefore the interference image captured by the camera is noisy. The goal of this experiment was to show that FBSA can eliminate the effect of contamination and will give us the correct interference pattern associated with the mirror. A schematic of the system is shown in FIG. 11 which is a Schematic of the experimental set up, two He—Ne lasers one at red wavelength (633 nm) and the other at green wavelength (543 nm) are coupled with each other using a coupler, the combined wave used as the input source of a Michelson interferometer, in one arm of the interferometer the rough sample is inserted and the interference field of the reflected light from sample and reference mirror captured by a monochromatic camera.

One serious difficulty was low interference contrast since the grimy mirror reflects light in all directions and only a small portion of it goes through the beam splitter and consequently reaches the camera. In the other hand almost 90% of the light will reflects back from the mirror to the camera. Therefore to avoid this problem, we placed a light attenuator in reference arm of the interferometer to balance the intensities.

Figure 12:
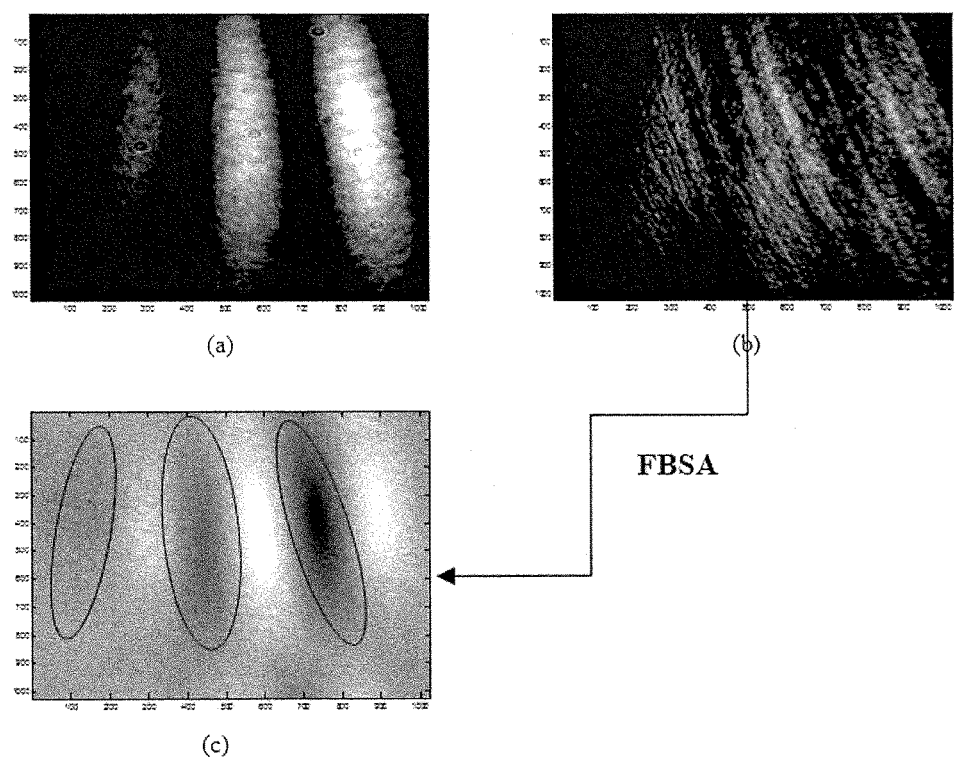
FIG. 12 illustrates Experimental results from the FBSA on Michelson interferometer.

Results:

The interference patterns of FIG. 12 illustrate two cases when both mirrors were clean (FIG. 12a) and when one mirror is covered by contamination (FIG. 12b). As it was expected the interference pattern of the grimy mirror shows rapid fluctuation in its intensity and no interference pattern can be detected from this signal. Therefore we applied FBSA to this signal and the result of the reconstructed fringe pattern is shown in FIG. 12c.

Industrial Film Thickness Measurement:

Based on the experimental results discussed herein, FBSA is a powerful noise reduction technique which can calculate the thickness of the film in the situations where the noise level is high. For example this technique can calculate the film's thickness with rough surfaces, contaminated surfaces, low reflective surfaces as well as paint and paper thickness measurements.

Biological Film Thickness Measurement:

One application of FBSA is in the diagnosis of the Dry Eye Syndrome (DES) by measuring the eye pre-corneal tear film thickness. The pre-corneal tear film in human's eyes is the outermost layer in the eye, which protects the cornea and provides lubrication for the ocular surface. One of the important characteristic of DES is the excessive evaporation of water from the tear film. This syndrome is one the most common ocular problems in humans which increase with aging. Various interferometric methods have been developed for tear film thickness measurement but since the interference pattern reflected back from the eye surface is very noisy and contains high amount of speckles which dominates the fringes, it is very difficult to rely on the result which has been extracted from the previous methods (add references). Fractional Bi-Spectrum Analysis can overcome this problem by reducing the noise and clear the image from the noise.

Surface Topography Measurement:

Based on the simulation results described herein, FBSA is a powerful technique to obtain the topography of objects with rough surface. This technique can be used in any existing laser interferometer by a slight modification in their input source.

Neglecting the Contamination Effect in Surface Topography Measurement:

Based on the experimental results described herein, FBSA is a powerful technique in laser interferometry, which can reduce the effect of contamination in such devices.

Blood Sugar Density Measurement:

Optical activity properties of the sugar molecules cause a phase shift in the linearly polarized light transmitted through the blood, therefore if the transmitted light interfere with the reference light, one should see the interference pattern caused by this phase shift. But usually since the transmitted wave has been affected by multiple scattering in the blood, the interference fringe pattern could not be detected. By using FBSA technique, we can extract the phase difference between these two waves and find the corresponding blood sugar density.

Finding the Doppler frequency for velocity measurement (both for biological and non-biological samples) is another application of FBSA technique.

Spatial Frequency Dependency of a Thin Film to its Thickness:

A laser beam coming out from a single mode fiber, which correspond to the theoretical TEM00 mode, generally has a Gaussian intensity profile. The complex electric field of a Gaussian beam can be mathematically expressed as:

$$E(r, Z) = E_0 \frac{\omega_0}{\omega(Z)} \exp\left(\frac{-r^2}{\omega^2(Z)} - ikZ - ik\frac{r^2}{2R(Z)}\right) \quad (13)$$

Where, $E_0$ is the field at $r=0$, $Z=0$, Z is the axial distance from the beam waist, r is the radial distance from the axis of the beam, $$k = \frac{2\pi}{\lambda}$$

is the wavenumber of the beam, $\omega_0$ is the Gaussian beam waist, $\omega(Z)$ is the radius of the beam spot at axial distance Z and $R(Z)$ is the beam curvature which is mathematically describe as:

$$R(Z) = Z\left[1 + \left(\frac{\pi\omega_0}{\lambda Z}\right)^2\right] \quad (14)$$

$$w(z) = w_0\sqrt{1 + \left(\frac{Z}{Z_R}\right)^2} \quad (15)$$

where, $$z_R = \frac{\pi w_0^2}{\lambda}$$

is the Rayleigh range and it is the range which the Gaussian wave front is approximately a plane wave.

Figure 13:
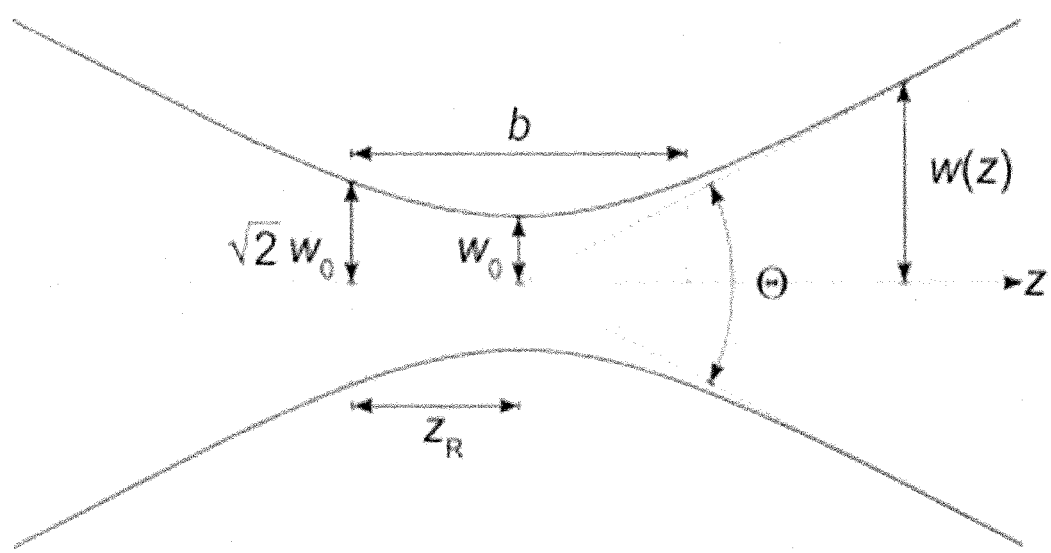
FIG. 13 illustrates Gaussian beam width w (z) as a function of the axial distance z. w0: beam waist; b: depth of focus; $Z_R$: Rayleigh range; θ: Total angular spread.
Figure 14:
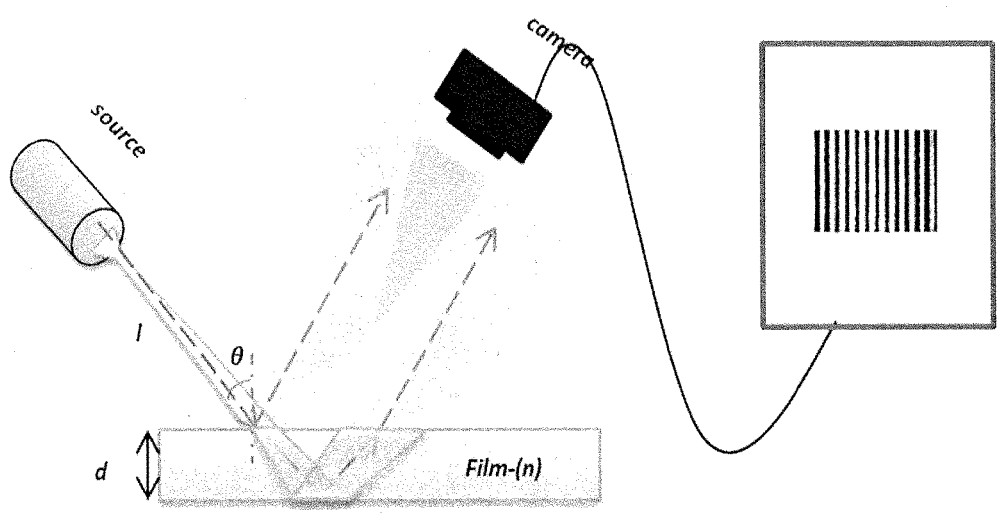
FIG. 14 illustrates an Interference pattern caused by the superposition of the Gaussian light from top and bottom surface of a film.

FIG. 13 is a Gaussian beam width w (z) as a function of the axial distance z. w0: beam waist; b: depth of focus; $Z_R$: Rayleigh range; θ: Total angular spread. When such a Gaussian beam hits a thin film, it reflects back from top and bottom surface of the film (FIG. 14). In the area where these two reflected beams are overlapping, the interference pattern is created due to the phase difference of the reflected fields and can be captured if a camera place on its direction.

Figure 15:
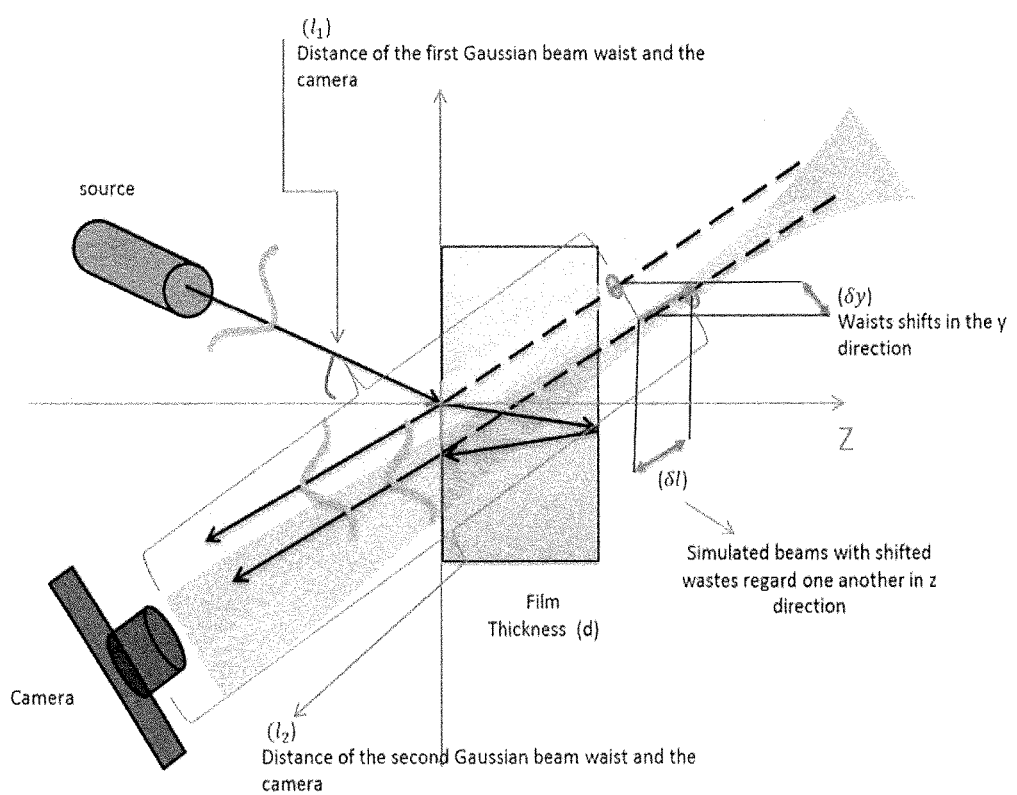
FIG. 15 illustrates Reflection from first and second interface of the film and simulated Gaussian beams associated with them with shifted waist regards one another.

Gaussian Beams Interference Reflected from a Thin Film:

We assume a two dimensional circular Gaussian beam incident at angle $\theta_i$ on a dielectric slab with thickness "d" and refractive index "n", surrounded by air. Therefore we have two reflected beams, one from the top surface of the slab and the other from bottom surface of the slab, FIG. 14. We can simulate the situation by considering two Gaussian beams coming from the other side of the film with parallel optical axis shifted relative to each other (FIG. 15). The waist of the beam reflected back from the bottom surface shifts in both Z and Y direction, which their values depend to the thickness of the film, its refractive index and the angle of Incident.

With some simple calculations and use of Snell's law we can find how much the optical axis of the second Gaussian beam is shifted related to the first one.

$$\delta l = 2nd\cos\theta_i \longrightarrow l_2 = l_1 + 2nd\cos\theta_i \quad (16)$$

-continued and, $$\delta y = \frac{2d\sin\theta_i}{\sqrt{n^2 - \sin^2\theta_i}} \quad (17)$$

where "n" and "d" are the refractive index and thickness of the film respectively and, "$\theta_i$" is the angle of incident. Therefore the two complex electric fields associated to the reflected beams from the film at the camera are:

$$E_1(r, l_1) = E_0 \frac{w_0}{w_1} \exp\left(\frac{-r_1^2}{w_1^2}\right) \exp\left(-ikl_1 + i\arctan\left(\frac{l_1}{z_R}\right)\right) \exp\left(-ik\frac{r_1^2}{2R_1}\right) \quad (18)$$

$$E_2(r, l_2) = E_0 \frac{w_0}{w_2} \exp\left(\frac{-r_2^2}{w_2^2}\right) \exp\left(-ikl_2 + i\arctan\left(\frac{l_2}{z_R}\right)\right) \exp\left(-ik\frac{r_2^2}{2R_2}\right) \quad (19)$$

The sum of these two fields at camera can be written as:

$$E^{total} = E_0 \frac{w_0}{w_1} \exp\left(\frac{-r_1^2}{w_1^2}\right) \exp\left(-ikl_1 + i\arctan\left(\frac{l_1}{z_R}\right)\right) \exp\left(-ik\frac{r_1^2}{2R_1}\right) + \quad (20)$$

$$E_0 \frac{w_0}{w_2} \exp\left(\frac{-r_2^2}{w_2^2}\right) \exp\left(-ikl_2 + i\arctan\left(\frac{l_2}{z_R}\right)\right) \exp\left(-ik\frac{r_2^2}{2R_2}\right)$$

Therefore the phase of these two filed at the camera is defined as:

$$\varphi_{E_1} = -kl_1 + \arctan\left(\frac{l_1}{z_R}\right) - k\frac{r_1^2}{2R_1} \quad (21)$$

$$\varphi_{E_2} = -kl_2 + \arctan\left(\frac{l_2}{z_R}\right) - k\frac{r_2^2}{2R_2} \quad (22)$$

The phase difference is a function of $l_1, l_2$, k, $$\frac{r_1^2}{R_1} \text{ and } \frac{r_2^2}{R_2}$$

which is defined as:

$$\delta\varphi = -k(\delta l) + \left[\arctan\left(\frac{l_1}{z_R}\right) - \arctan\left(\frac{l_2}{z_R}\right)\right] - \frac{k}{2}\left(\frac{r_1^2}{R_1} - \frac{r_2^2}{R_2}\right) \quad (23)$$

For any Gaussian beam with fixed incident angle, fix distance between the camera and the top surface of the film and a fix film thickness, the first two terms of equation 22 are constant, therefore at any arbitrary plane of camera, the phase changes as a function of $r_1$ and $r_2$:

$$\varphi = \varphi_0 - \frac{k}{2}\left(\frac{r_1^2}{R_1} - \frac{r_2^2}{R_2}\right) \quad (24)$$

$$\text{where, } R_2 \approx R_1\left(1 + \frac{2nd}{l_1}\cos\theta_i\right) \quad (25)$$

For thin films where, $d \ll l_1$, $R_2 \cong R_1$, we have:

$$\varphi = \varphi_0 - \frac{k}{2}\frac{1}{R}(r_1^2 - r_2^2) \quad (26)$$

In order to find how $r_1^2$ and $r_2^2$ are related to each other, we need to find the relation between the centers of two reflected spots on the camera plane. For simplicity we have focused the camera on the top surface of the film. Therefore by applying Snell's law and some simple calculations one can easily find that centers of two spots on the film are apart from each other by:

$$\delta x = \frac{2d\sin\theta\cos\theta}{\sqrt{(n^2 - \sin^2\theta)}} \quad (27)$$

Figure 16:
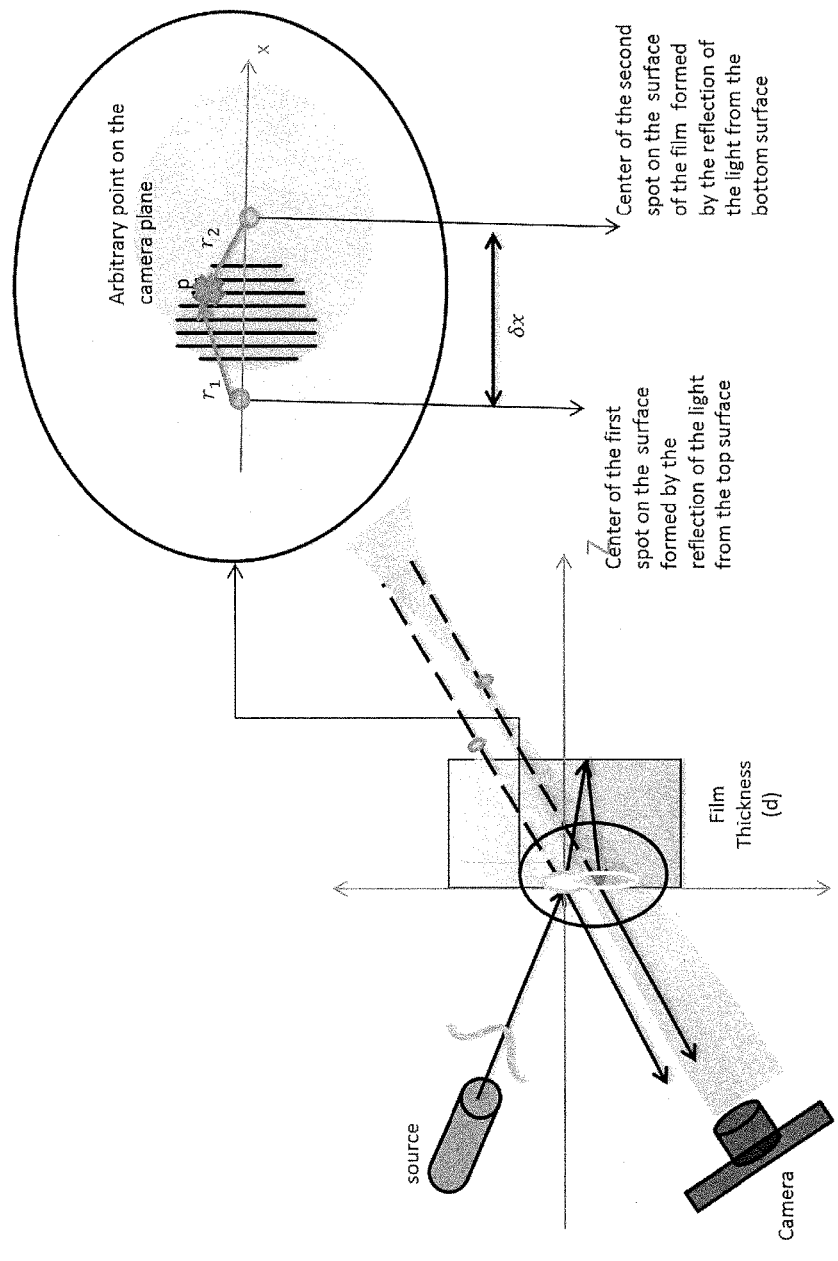
FIG. 16 illustrates Two reflected beam spots on the camera plane and the interference pattern in their overlap area.

FIG. 16 illustrates two reflected beam spots on the camera plane and the interference pattern in their overlap area. At any arbitrary point in the camera plane we have:

$$r_1^2 - r_2^2 = -\delta x^2 - 2x\delta x \quad (28)$$

Where the origin chosen to be the center of the first spot (reflected from the top surface). For thin films, $\delta x \ll x$, so we can ignore the first term "$\delta x^2$", therefore:

$$r_1^2 - r_2^2 = -2x\delta x \quad (29)$$

FIG. 16 illustrates two reflected beam spots on the camera plane and the interference pattern in their overlap area. By substituting equation 27 on equation 23, the phase on the camera plane varies as a function of x and it depends on the wave curvature ($R_1 = R$) and the wavenumber (k) as below.

$$\varphi(x) = \varphi_0 + \frac{k}{2}\frac{1}{R}(2x\delta x) \quad (17)$$

The distance between two consecutive bright or dark fringes is called the spatial period of the interference pattern as the phase varies by $2\pi$, therefore:

$$\varphi(x_1) - \varphi(x_2) = 2\pi \quad (18)$$

Figure 17:
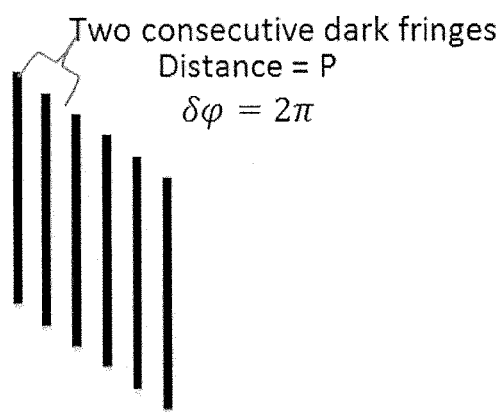
FIG. 17 illustrates Phase difference between two consecutive dark or bright fringes is equal to 2π.

FIG. 17 illustrates Phase difference between two consecutive dark or bright fringes is equal to $2\pi$. Therefore for two consecutive fringes, we have:

$$2\pi = \frac{k}{2}\frac{1}{R_1}(2\delta x)P \quad (19)$$

where, P is the period of the signal. By substituting the value of $\delta x$ in the above formula, the relation between the thickness of the film and the frequency of the interference pattern can be obtained:

$$d = \frac{\lambda R * \sqrt{(n^2 - \sin^2\theta)}}{2n * \sin\theta\cos\theta} * F \quad (20)$$

Where F is the frequency of the interference pattern, $$F = \frac{1}{P},$$

"λ" is the wavelength, R is the radius of the beam curvature at the top surface of the film and is defined as $$R_1 = l_1 * \left[1 + \left(\frac{Z_R}{l_i}\right)^2\right],$$

where $l_1$ is the axial distance between the waist of the beam and top surface of the film, n is the refractive index of the film, and θ is the incident angle.

Therefore for a specific source with known wavelength and waist, the thickness of a specific film is directly proportional to the frequency of the interference pattern multiply by a constant, which can be extracted by calibrating the system.

Therefore for two consecutive fringes, we have $$2\pi = \frac{k}{2}\frac{1}{R_1}(2\delta x)P \qquad (21)$$

where, P is the period of the signal.

By substituting the value of δx in the above formula, the relation between the thickness of the film and the frequency of the interference pattern can be obtained:

$$d = \frac{\lambda R * \sqrt{(n^2 - \sin^2\theta)}}{2n * \sin\theta\cos\theta} * F \qquad (22)$$

Where F is the frequency of the interference pattern, F=1/p, λ is the wavelength, R is the radius of the beam curvature at the top surface of the film and is defined as:

$$R_1 = l_1 * \left[1 + \left(\frac{Z_R}{l_i}\right)^2\right] \qquad (23)$$

where $l_1$ is the axial distance between the waist of the beam and top surface of the film, is the refractive index of the film, and is the incident angle.

Therefore for a specific source with known wavelength and waist, the thickness of a specific film is directly proportional to the frequency of the interference pattern multiply by a constant, which can be extracted by calibrating the system. We simulated the superposition of two Gaussian beams reflected from top and bottom surfaces of a thin film at different thicknesses using MATLAB.

Simulation:

In this simulation we investigated the interference pattern of two Gaussian beams with shifted waists. The shift of the waists depends on the thickness of the film and the incident angle. The corresponding wavelength is 633 nm, the refractive index is 1.5, the initial incident angle is 30 degree and the distance between the waste of the first simulated beam and the image plane (which is focused on the top surface of the film) is 40 mm. The results are shown below for the films with thicknesses of 200 micron to 10 microns.

Figure 18:
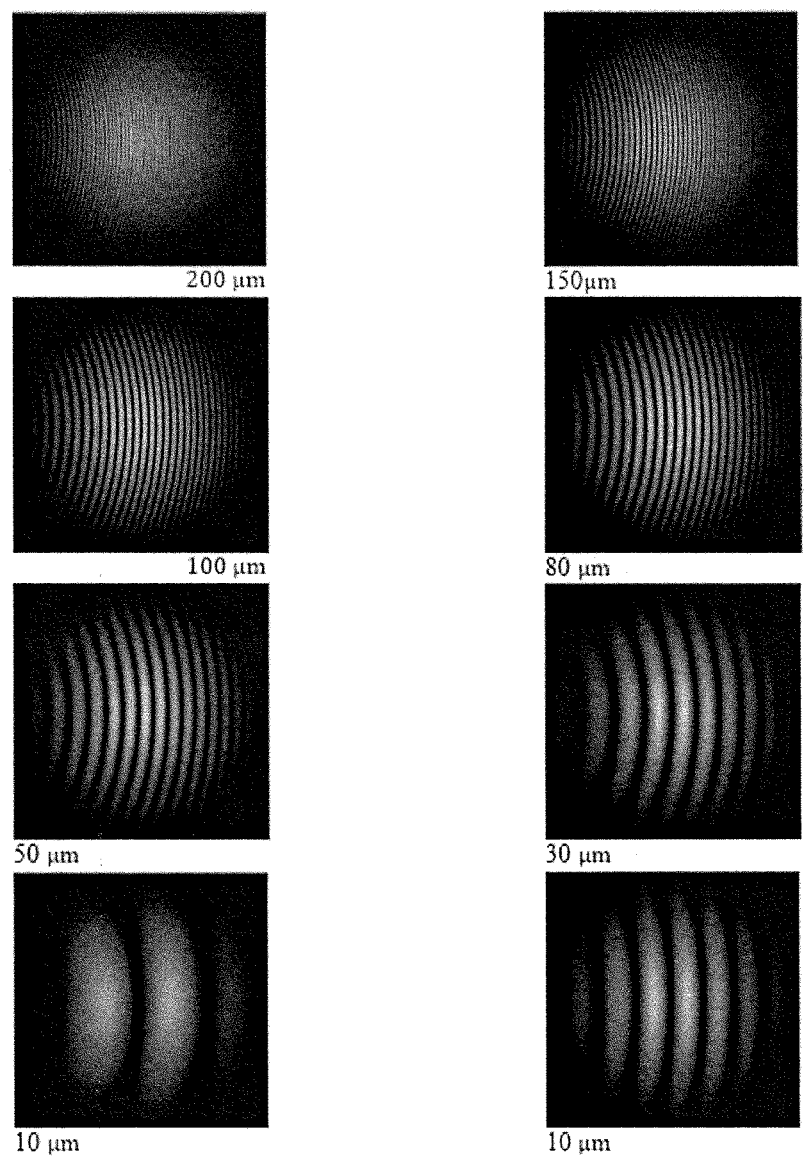
FIG. 18 illustrates results of the simulation showing as the thickness of the film decreases, the number of fringes decreases respectively.

FIG. 18 illustrates Results of the simulation shows as the thickness of the film decreases, the number of fringes decreases respectively, for a film with thickness 10 μm, with the above configuration only 2-3 fringes formed, this fact limits the accuracy of our measurement so we need to change the configuration in order to obtain more fringes from the thinner films. In order to get more fringes we first change the incident angle from 30 degree to 70 degree.

Fourier Spectrum

One of the well-known techniques of measuring the film thickness is utilizing the Fourier transform on interference pattern made by the superposition of two reflected light from top and bottom surfaces of the film, and find the interference pattern frequency which relates to the film thickness. This method can give an accurate value for the film thickness in the situation where the noise level of the system is low compare to the signal level and we have a relatively clean and observable interference pattern captured by the camera.

Figure 19:
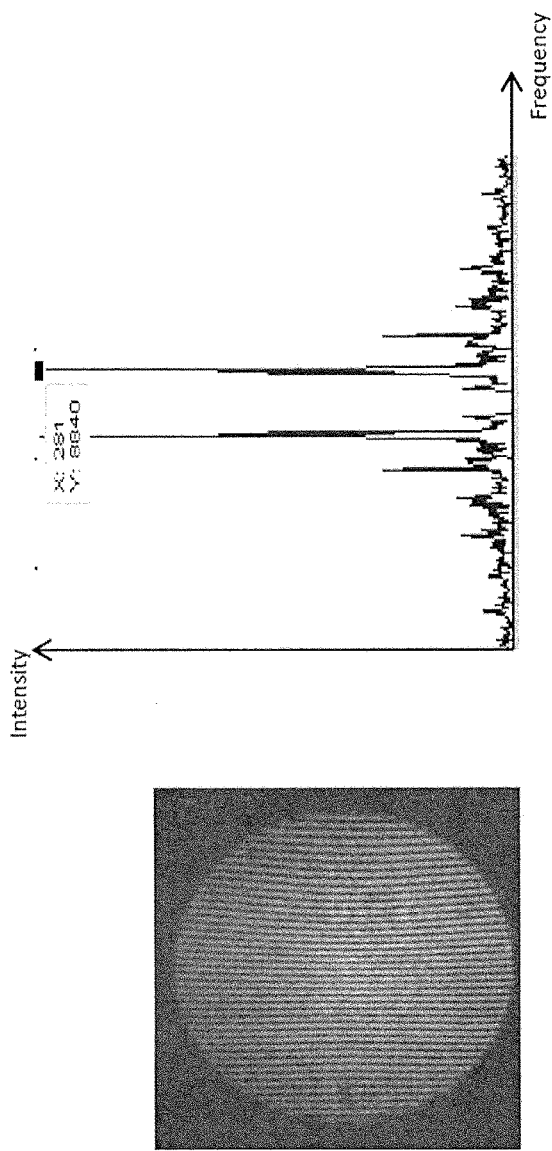
FIG. 19 illustrates Reflected image captured by the camera from the clean glass wafer and its Fourier Spectrum; the Fourier spectrum shows a peak at a specific frequency which indicates the exact value of the number frequency of the captured periodic pattern.

FIG. 19 shows that the Fourier spectrum of the image gives an accurate value for the frequency of the interference pattern, therefore one can simply find the thickness of the film using the obtained equation of thickness (equation 22) and knowing the experimental parameters such as refractive index of the film, the angle of incidence, wavelength, etc.

Figure 20:
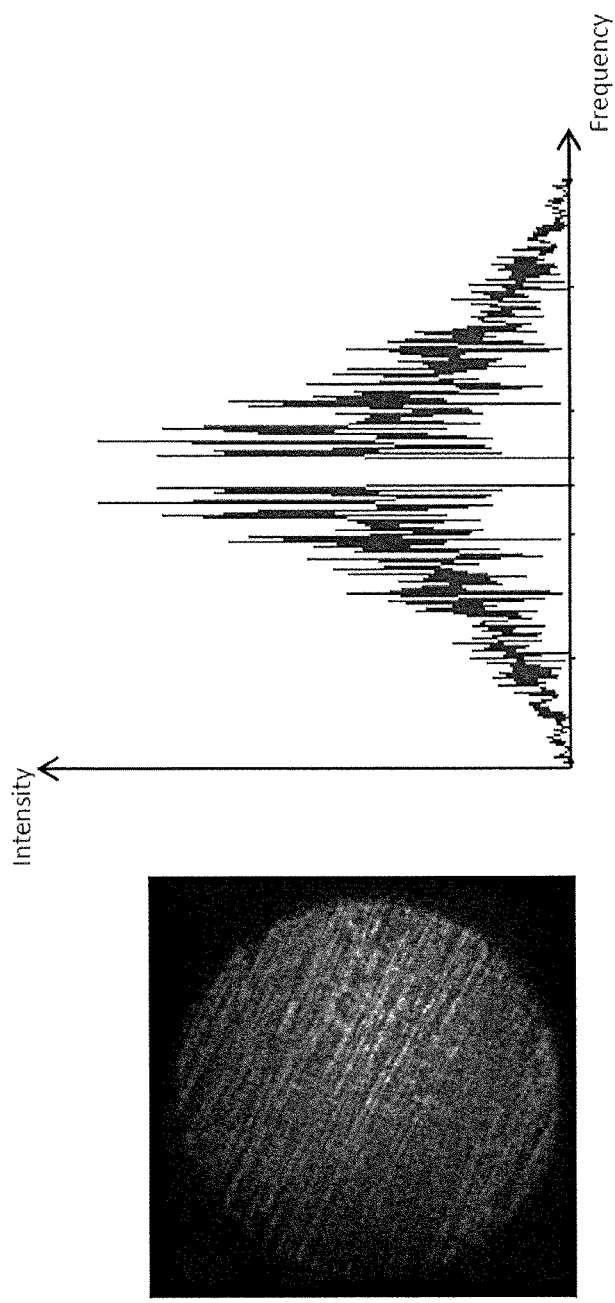
FIG. 20 illustrates Reflected image captured by the camera from the etched-glass wafer and its Fourier spectrum; In the Fourier spectrum, the signal is completely covered by the noise and no useful information can be extracted.

But in most real situations, the level of noise is very high compare to the signal level and basically no interference pattern can be seen in the reflected pattern captured by the camera, therefore finding an accurate value for the frequency of the interference pattern will be relatively difficult and sometimes impossible (FIG. 20). Therefore an alternative technique is needed to extract the signal out of the dominant noise. Fractional bi-spectrum is a fast and accurate method, which can significantly reduce the noise level of the system and extract the frequency information out of a very noisy pattern. In the next section we will describe the basic concept of this method and show some of the improved result from the simulation and experiments by applying this technique.

Again, In order to apply fractional bi-spectrum, we need at least two frequency components in the captured image by the camera. The frequency of each interference pattern is related to the thickness of the film and the wavelength of the associated source. Therefore the 2-D signal (image) captured by the camera in the absence of noise almost has the mathematical form of:

$$I(x,y)=a(x,y)+b(x,y)\cos(a_{1x}x+a_{1y}y)+c(x,y)\cos(b_{2x}x+b_{2y}y) \qquad (24)$$

Where, a(x, y), b(x, y), c(x, y) represent the irradiance variation arising from the non-uniform light reflected by the test object, and "$a_{1x}$", "$a_{1y}$", "$b_{2x}$", and "$b_{2y}$" are spatial angular frequencies of the patterns for wavelengths 1 and 2 in both x and y direction.

Figure 21:
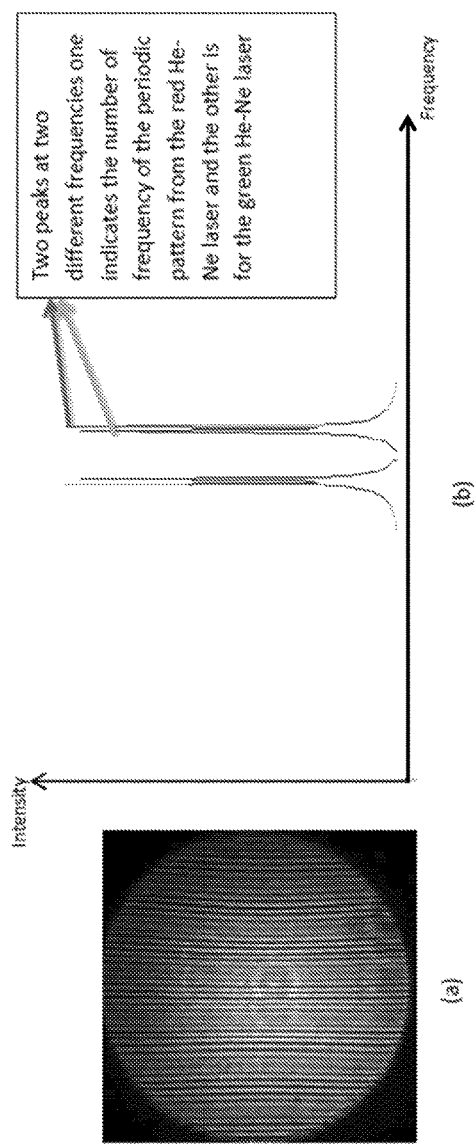
FIG. 21 illustrates (a) Reflected image captured by the camera from a clean glass wafer illuminated by red and green He—Ne lasers simultaneously (b) the Fourier spectrum of an arbitrary horizontal line of the image, in the Fourier spectrum there are two peaks which indicate frequencies for the red and green interference pattern.

FIG. 21 is (a) Reflected image captured by the camera from a clean glass wafer illuminated by red and green He—Ne lasers simultaneously (b) the Fourier spectrum of an arbitrary horizontal line of the image, in the Fourier spectrum there are two peaks which indicate frequencies for the red and green interference pattern.

For the sake of simplicity, all the computations have been done on one vertical and one horizontal line from the 2D signal; therefore we have two one dimensional signals in x and y directions:

$$I(x)=a(x)+b(x)\cos(a_{rx}x)+c(x)\cos(b_{gx}x)$$

$$I(y)=a(y)+b(y)\cos(a_{ry}y)+c(y)\cos(b_{gy}y)$$

Indices r and g represent wavelengths 1 (red) and 2 (green), which we have used in our experiments. By applying the fast Fourier transform algorithm on we can find the Fourier spectrum of these two signals:

$$\mathcal{F}\{I_x(x)\} = A_x(f_x) + \frac{1}{2}\left\{B_x\left(f_x - \frac{a_{rx}}{2\pi}\right) + B_x\left(f_x + \frac{a_{rx}}{2\pi}\right)\right\} +$$
$$\frac{1}{2}\left\{C_x\left(f_x - \frac{b_{gx}}{2\pi}\right) + C_x\left(f_x + \frac{b_{gx}}{2\pi}\right)\right\}$$

$$\mathcal{F}\{I_y(y)\} = A_y(f_y) + \frac{1}{2}\left\{B_y\left(f_y - \frac{a_{ry}}{2\pi}\right) + B_y\left(f_y + \frac{a_{ry}}{2\pi}\right)\right\} +$$
$$\frac{1}{2}\left\{C_y\left(f_y - \frac{b_{gy}}{2\pi}\right) + C_y\left(f_y + \frac{b_{gy}}{2\pi}\right)\right\}$$

Where the capital letters denote the Fourier spectra and is the spatial frequency in x and y direction associated to each wavelength. Therefore there are four spatial frequency components for each of the Fourier spectra of FI(X) and FI(Y). Since the relation between the two wavelengths is known, we can simply find the relation between the frequency components in the frequency domain.

$$\lambda_{red} = \lambda_{green} + k \times \lambda_{green}$$

Where "k" is a constant and can be derived from the relation between wavelengths of two lasers.

The associated frequency components in the Fourier spectrum are related to each $$f_{red} = \left(\frac{1}{1+k}\right) f_{green}$$
and;
$$f_{green} = (1+k) f_{red}$$

Fractional bi-Spectrum can be calculated by the following equation:

$$B^F(f_1, f_2, k) = \frac{1}{T} \lim_{T \to \infty} \langle \mathcal{F}I(f_1) \times \mathcal{F}I(f_2) \times \mathcal{F}I^*(f_1 + kf_2) \rangle$$

Where; "FI(f)" is the Fourier transform of the signal.

As it is shown, FBS is the expectation value of product of three frequency components in the Fourier domain over the whole spectral range. The discrete Fractional bi-spectrum can be defined by following equation:

$$B^F[f_i, f_j, k] = \frac{1}{MN} \sum_{i=1}^{N} \sum_{j=1}^{M} \mathcal{F}I[f_i] \times \mathcal{F}I[f_j] \times \mathcal{F}I^*[f_i + kf_j]$$

Fractional bi-spectrum of a 1D signal is a 2D signal which for our signal is mathematically always zero except the case where $f_i = f_j = f_r$ and $f_g = f_r + kf_r$. k is the fractional bi-spectrum constant and defines how the signal frequency components at two implemented wavelength are related to each other.

Therefore if one looks only over the diagonal axis of the fractional bi-spectrum plane, where, there would be a sharp peak at frequency of or which both are related to the thickness of the film. Since the speckle noise components do not have such an exact relation to one another, applying the Fractional Spectrum Analysis on a noisy signal reduces the noise of the signal and we can easily extract the signal from the noise.

This method has been confirmed both by simulations and experiments. Experimental results show that this method is applicable when noise dominates the signal where no other methods can extract the signal from the noise.

Figure 22:
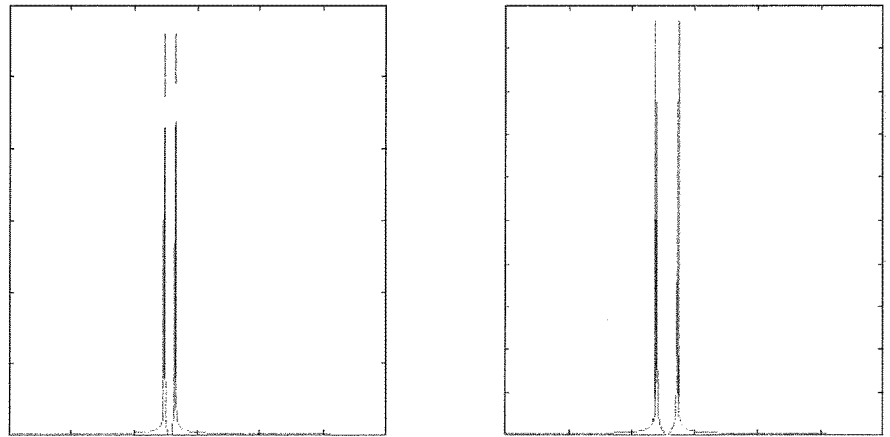
FIG. 22 illustrates Fourier spectrum of the simulated sinusoidal signal in x and y directions in the absence of the noise.
Figure 23:
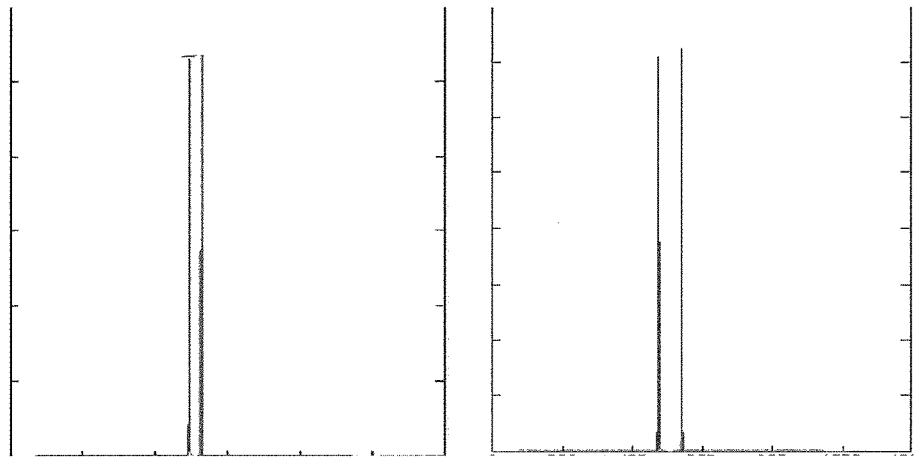
FIG. 23 illustrates Fractional bi-spectrum of the simulated signal in x and y directions. Fractional bi-spectrum gives the same frequency components in x and y direction as the Fourier spectrum does for the signal with no noise.
Figure 24:
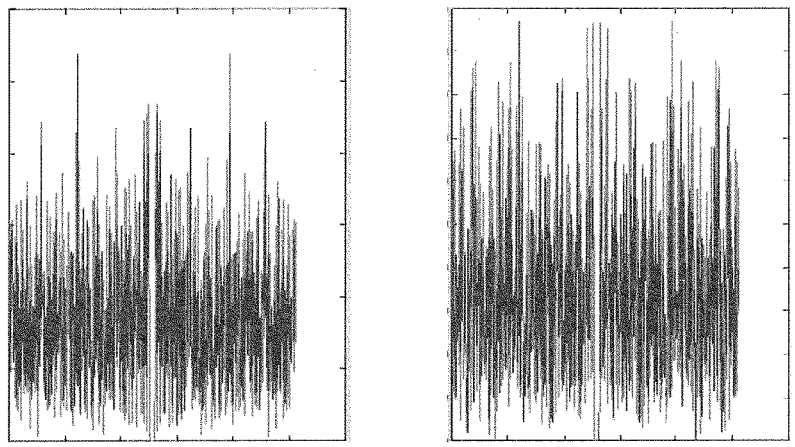
FIG. 24 illustrates Fourier spectrum of the simulated signal with the presence of additive Gaussian noise in the x and y directions Fourier spectrum does not reveal any information about the signal and the number of frequency.
Figure 25:
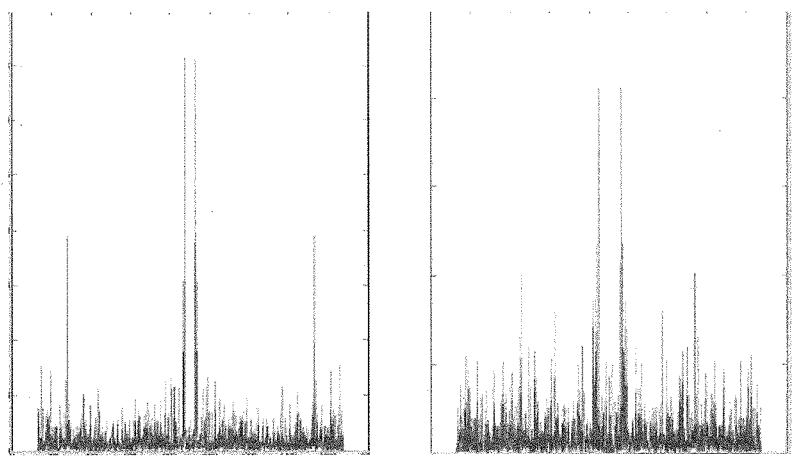
FIG. 25 illustrates Fractional bi-spectrum of the simulated signal in the presence of the additive Gaussian noise in the x and y directions; Fractional bi-spectrum clearly reduces the noise and extracts the signal out of noise and reveals the frequency value.
Figure 26A:
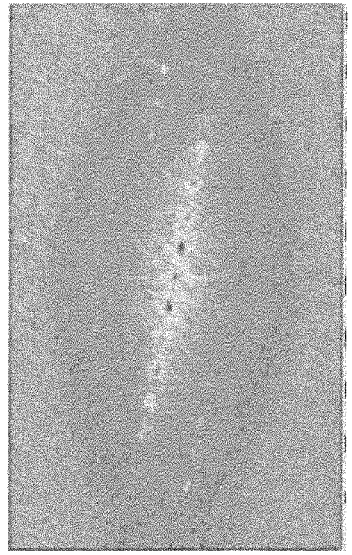
FIG. 26A illustrates Captured reflected pattern from the glass wafer, its Fourier spectrum, and fractional bi-spectrum in x and y directions.
Figure 26A:
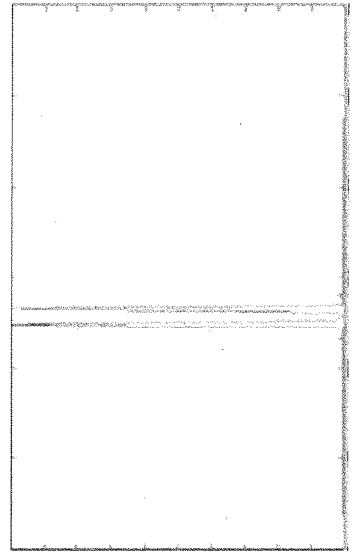
Figure 26A:
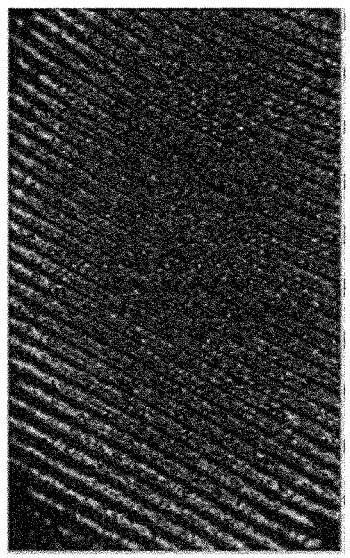
Figure 26A:
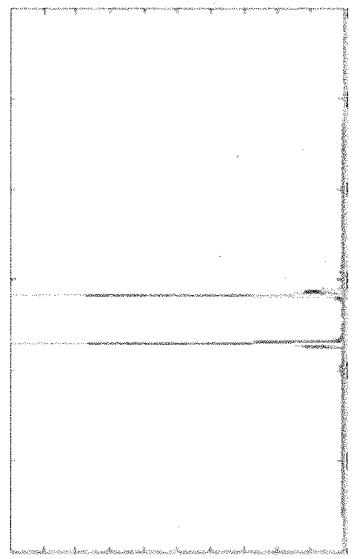
Figure 26B:
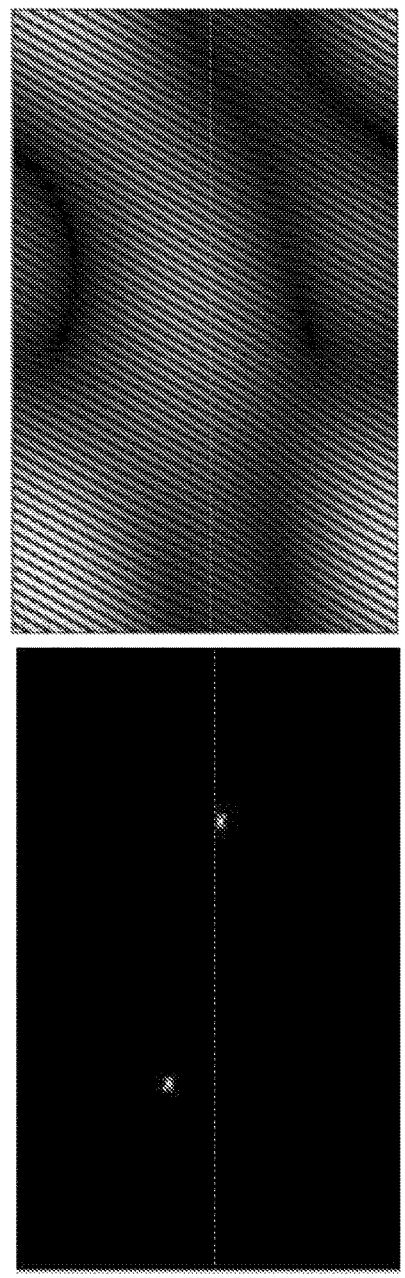
FIG. 26B illustrates Filtered Fourier spectrum of the image around the obtained frequency by FBSA, and reconstructed interference pattern.
Figure 27A:
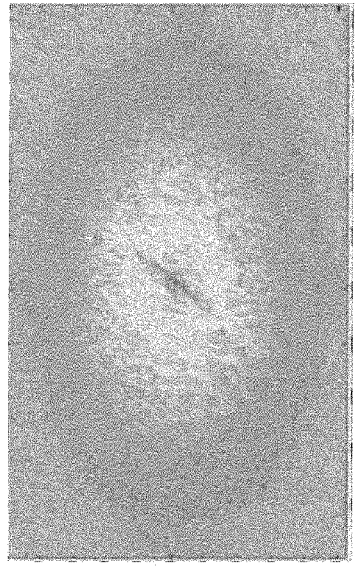
FIG. 27A illustrates Captured reflected pattern from the very rough etched glass wafer, its Fourier spectrum, and fractional bi-spectrum in x and y directions.
Figure 27A:
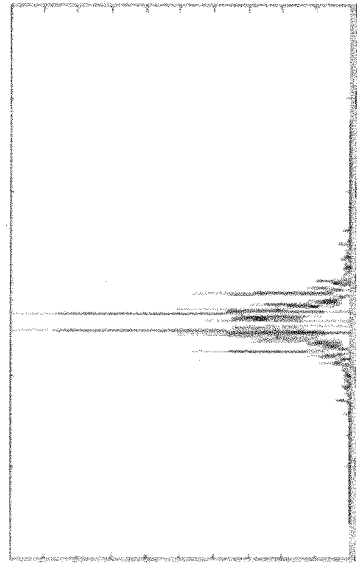
Figure 27A:
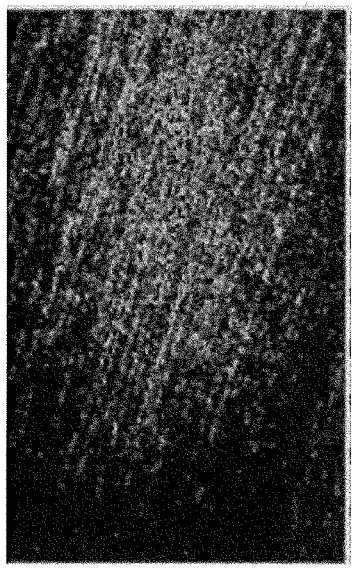
Figure 27A:
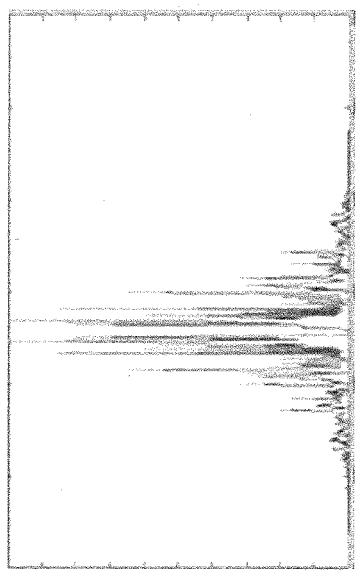
Figure 27B:
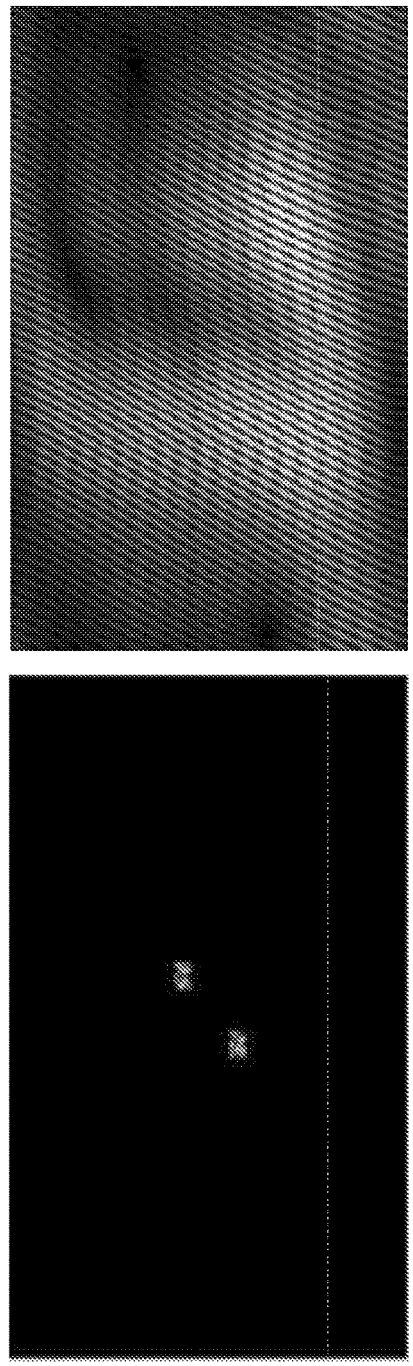
FIG. 27B illustrates Filtered Fourier spectrum of the image around the obtained frequency by FBSA, and reconstructed interference pattern of the etched glass wafer.
Figure 28A:
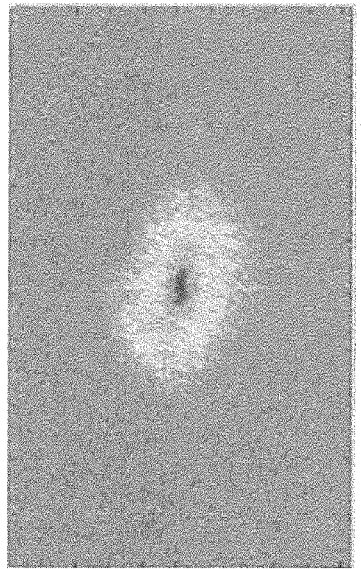
FIG. 28A illustrates Captured reflected pattern from the solder bump coating position 1, its Fourier spectrum, and fractional bi-spectrum in x and y directions.
Figure 28A:
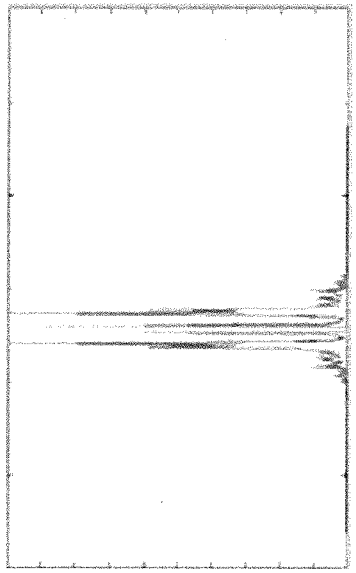
Figure 28A:
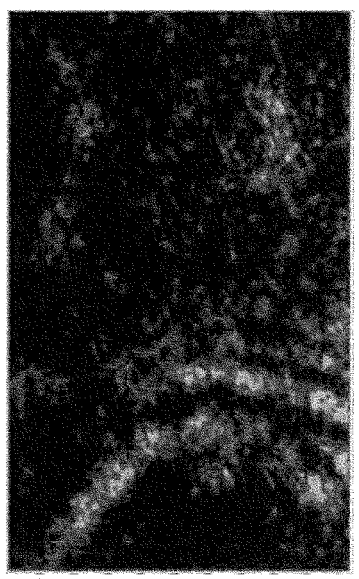
Figure 28A:
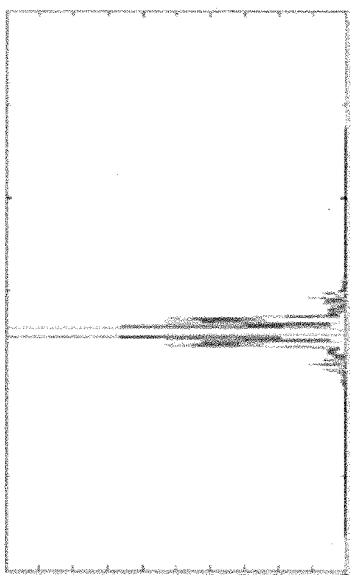
Figure 28B:
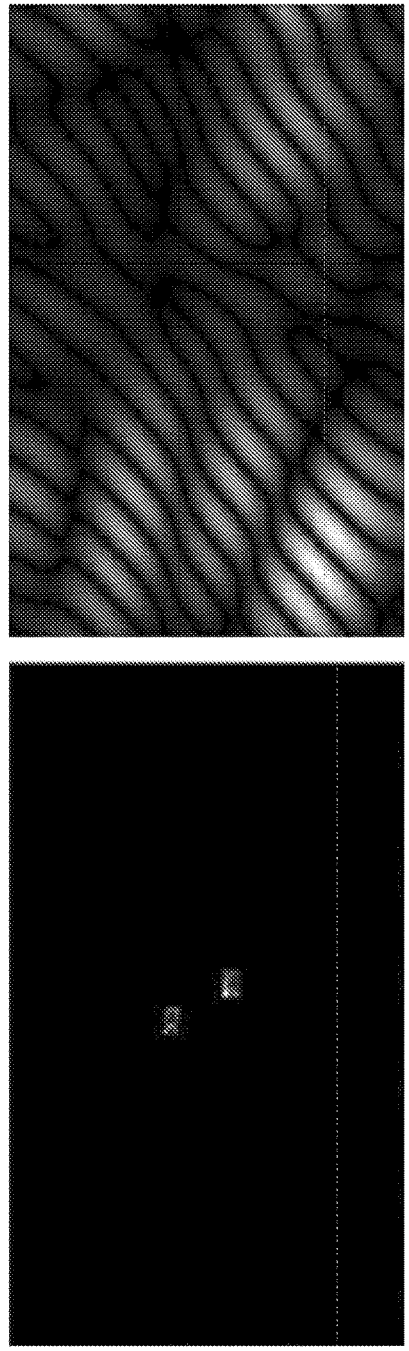
FIG. 28B illustrates Filtered Fourier spectrum of the image around the obtained frequency by FBSA, and reconstructed interference pattern of the solder bump coating.
Figure 29A:
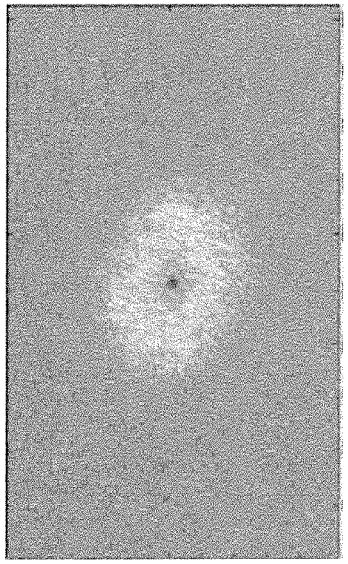
FIG. 29A illustrates Captured reflected pattern from the solder bump coating position 2, its Fourier spectrum, and fractional bi-spectrum in x and y directions.
Figure 29A:
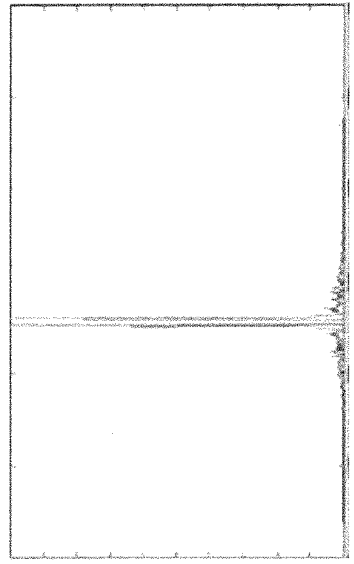
Figure 29A:
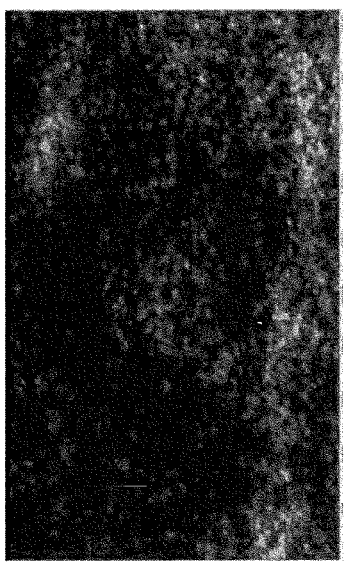
Figure 29A:
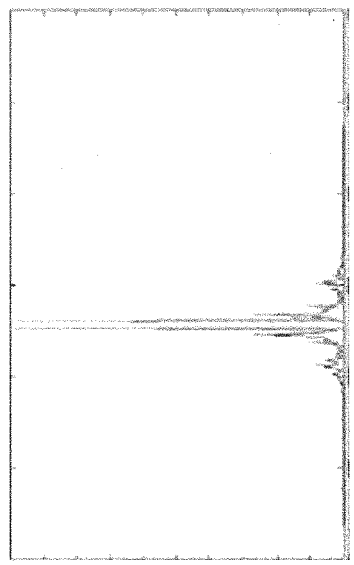
Figure 29B:
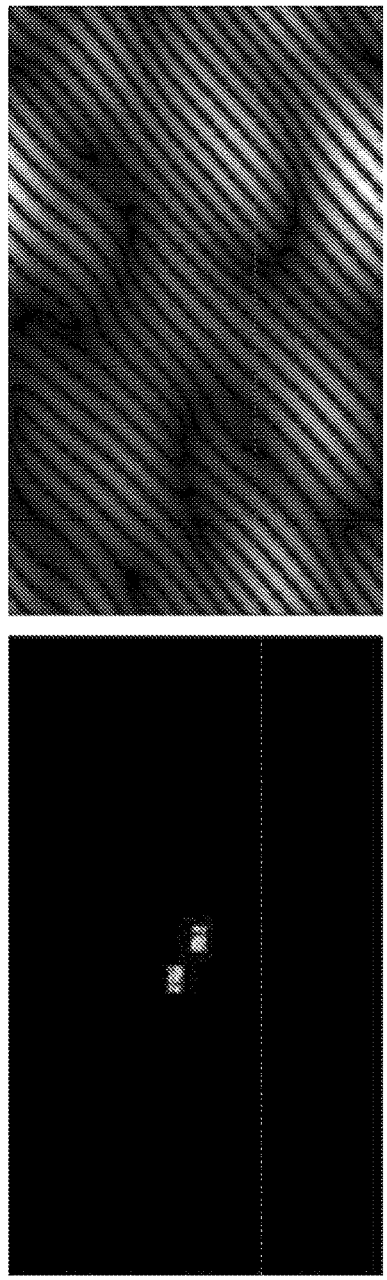
FIG. 29B illustrates Filtered Fourier spectrum of the image around the obtained frequency by FBSA, and reconstructed interference pattern of the solder bump coating.
Figure 30A:
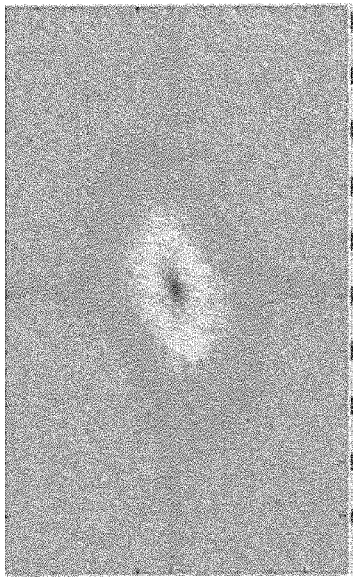
FIG. 30A illustrates Captured reflected pattern from a tape sheet, its Fourier spectrum, and fractional bi-spectrum in x and y directions.
Figure 30A:
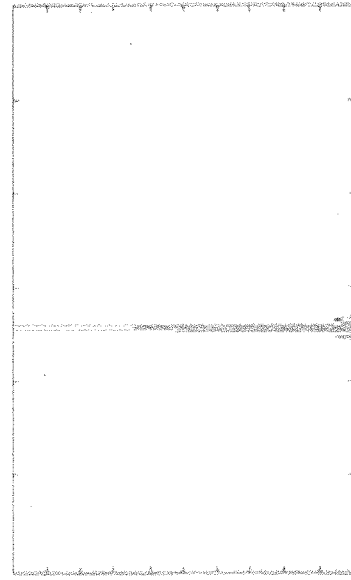
Figure 30A:
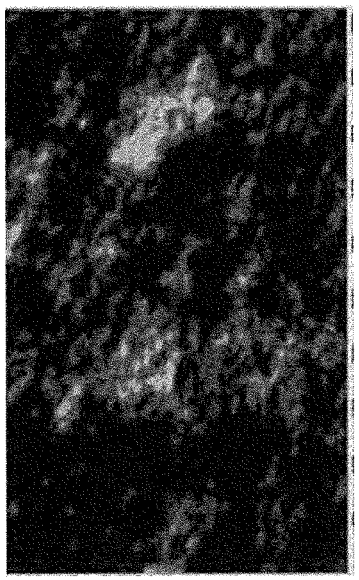
Figure 30A:
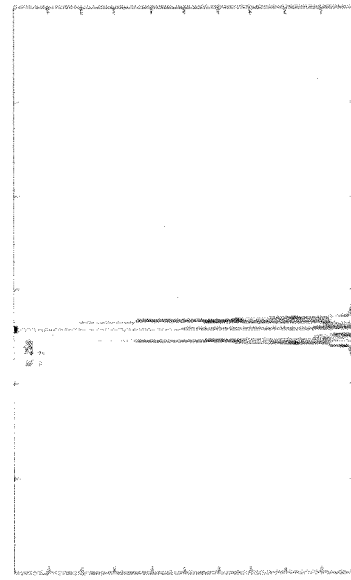
Figure 30B:
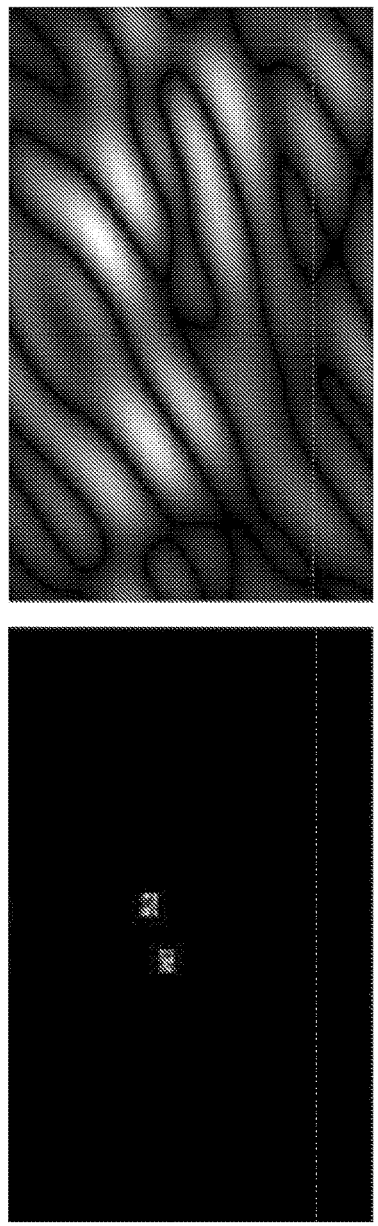
FIG. 30B illustrates Filtered Fourier spectrum of the image around the obtained frequency by FBSA, reconstructed interference pattern of the tape, and frequency components of the reconstructed pattern in x and y directions.

FIG. 22 shows the Fourier spectrum of a signal with no noise applied. The fractional bi-spectrum method also provides the same frequency contents as shown in FIG. 23. FIG. 24 is the Fourier transform of a signal where the noise level is increased significantly. As one can see the frequency content of the signal is not easily detectable. Fractional bi-spectrum technique has been applied to the same signal and results are presented in FIG. 25. The spatial frequency contents in both "x" and "y" directions appear very clearly.

In most real situations such as biological samples, Fourier spectrum of the reflected image contains high level of noise, which makes it difficult to extract the signal out of the dominant noise. We have applied the fractional bi-spectrum technique to the image which is the reflection pattern from a very rough etched glass, the reflected pattern of the solder bumps coating at two different positions and the reflected pattern of a tape. As it is shown below, the reflected pattern captured from these objects contain high level of noise, which make it impossible to extract any information from their Fourier spectrum. In all these cases by applying fractional bi-spectrum technique we could extract the signals' frequencies components in both x and y directions, accurately. We filtered the two dimensional Fourier spectrum of the reflected pattern around the obtained frequency by FBSA and reconstructed the image for each sample. In the reconstructed image, the periodic pattern is emerged and one can easily find its frequency and phase profile of the sample of interest. In the FIGS. 26 through 30, the reflected captured image by the camera, its Fourier spectrum, FBSA in x and y directions, the filtered Fourier spectrum of the image around the obtained frequency detected by fractional bi-spectrum technique and the clear reconstructed image are shown for four different samples. These results show that FBSA is a very practical and reliable method to detect the signal at the presence of high noise level.

In order to make sure this technique works properly, we first used a clean interference pattern captured from a clean glass wafer as the reference. The results show that FBSA can detect the signal and reconstruct the period pattern. The reconstructed periodic pattern from FBSA is in agreement with the original interference pattern.

We have applied FBSA on the very rough etched glass wafer, a solder bump coating at two different locations with different thicknesses and a tape sheet. The results show FBSA can extract the desired information from the noise in all of this situations.

The Fractional Bi-Spectrum Analysis (FBSA) is a noise reduction technique which can be directly used for film thickness measurement and it is specifically important for the situations where the noise in the system is significant and the signal of interest is covered by the noise. One application of this method is in the diagnosis of the Dry Eye Syndrom (DES) by measuring the eye pre-corneal tear film thickness [15]. The pre-corneal tear film in human's eyes is the outermost layer in the eye which protects the cornea and provide lubrication for the ocular surface. One of the important characteristic of DES is the excessive evaporation of water from the tear film. This syndrome is one the most common ocular problems in humans which increase with aging. Various interferometric methods have been developed for tear film thickness measurement but since the interference pattern reflected back from the eye surface is very noisy and contains high amount of speckles which dominates the fringes, it is very difficult to rely on the result which has been extracted from the previous methods (add references). Fractional Bi-Spectrum Analysis can overcome this problem by reducing the noise and clear the image from the noise.

Another application of the FBSA is in the interferometry. We can apply FBSA on the interferogram with speckle noise. Fractional bi-spectrum analysis can clean each interference pattern from the speckle noise so that phase measurement become possible. In this case laser interferometry could be applied to specular surfaces.

Another application is the blood sugar density measurement. Optical activity properties of the sugar molecules cause a phase shift in the linearly polarized light transmitted through the blood, therefore if the transmitted light interfere with the reference light, one should see the interference pattern caused by this phase shift. But usually since the transmitted wave has been affected by multiple scattering in the blood, the interference fringe pattern could not be detected. By using FBSA technique, we can extract the phase difference between these two waves and find the corresponding blood sugar density.

Finding the Doppler frequency for velocity measurement (both for biological and non-biological samples) is another application of FBSA technique.

Variously, the present disclosure presents: 1. A novel noise reduction mechanism, fractional bi-spectrum, for optical and electrical signals (FSB.); 2. A novel noise reduction mechanism, fractional cross-correlation, for optical and electrical signals (FCC.); 3. A method for measuring the thickness of the films including those with rough surfaces using FBSA; 4. A contact method for measuring the thickness of the films including those with rough surfaces using FCC; 5. A method for measuring the films with contaminated surfaces using FBSA; 6. A method for measuring the films with contaminated surfaces using FCC; 7. A non-invasive method for measuring the surface topography of rough surfaces using FBSA; 8. A non-invasive method for laser interferometery of objects with contamination using FBSA; 9. A method to determine the Doppler frequency using FSBA; 10. A method to determine the Doppler frequency using FCC; 11. A method to determine blood sugar using FSBA; 12. A method to determine blood sugar using FCC; 13. A method to measure thickness of paints using F SBA; 14. A method to measure thickness of paints using FCC; 15. A method to measure thickness of papers using FSBA; and 16. A method to measure thickness of papers using FCC.

REFERENCES (INCORPORATED HEREIN BY REFERENCE)

[1] M J. Ireland; G. J. Robertson; P. G. Tuthill; B. A. Warrington, "Low-cost scheme for high-precision dual-wavelength laser metrology". APPLIED OPTICS, 52(12): 2808-2814, (2013)

[2] PERINI, U; TIZIANI, H, "A COMBINED DISTANCE AND SURFACE PROFILE MEASUREMENT SYSTEM FOR INDUSTRIAL APPLICATIONS"—A EUROPEAN PROJECT, MEASUREMENT SCIENCE & TECHNOLOGY, 5(7):807-815, (1994)

[3] D W D W Blodgett, "Applications of laser-based ultrasonic to the characterization of the internal structure of teeth". JOURNAL OF THE ACOUSTICAL SOCIETY OF AMERICA, 114(1):542-9, (2003)-7

[4] Schmitt, J. M., "Optical coherence tomography (OCT): a review," Selected Topics in Quantum Electronics, IEEE Journal of, vol. 5, no. 4, pp. 1205, 1215, July/August (1999)

[5] Rosen, P. A.; Hensley, S.; Joughin, I. R.; Fuk K. Li; Madsen, S. N.; Rodriguez, E.; Goldstein, Richard M., "Synthetic aperture radar interferometry", Proceedings of the IEEE, vol. 88, no. 3, pp. 333, 382, March (2000)

[6] Z. Changming; N. Jun; L. Yanbo; Guochang Gu, "Speckle Noise Suppression Techniques for Ultrasound Images," Internet Computing for Science and Engineering (ICICSE), 2009 Fourth International Conference on, vol., no., pp. 122, 125, 21-22, (2009)

[7] Leendertz, J. A. "Interferometric displacement measurement on scattering surfaces utilizing speckle effect", J. Phys. E: Sci. Instrum. 3, 214-218, (1970)

[8] D. P. Popescu, M. D. Hewko, M. G. Sowa, Optics Communications, 269, (2007) 247

[9] Y. Rangsanseri, W. Prasongsook, 9th International Conference on Neural Information Processing, Singapore, pp. 792-795, November (2002)

[10] E. Moschetti, M. G. Palacio, M. Picco, et al., Latin American Applied Research 36 (2006) 115

[11] C. Tauber, P. Spiteri, H. Batatia, Applied Numerical Mathematics 60 (2010) 1115.

[12] D. Kerr, F. M. Santoyo, and J. R. Tyrer, "Manipulation of the Fourier components of speckle fringe patterns as a part of an interferometric analysis process," J. Mod. Opt. 36, 195-203 (1989)

[13] J. W. Goodman, Speckle Phenomena in Optics: Theory and Applications 1st ed. (Ben Roberts, 2007).

[14] Hoshino, K.; Sumi, H.; Nishimura, T., "Noise Detection and Reduction for Image Sensor by Time Domain Auto-correlation Function Method," Industrial Electronics, 2007. ISLE 2007, IEEE International Symposium on, vol., no., pp. 1737, 1740, 4-7 June (2007)

[15] K. Azartash; J. Kwan; J. R. Paugh; et al, "Pre-corneal tear film thickness in humans measured with novel technique", Molecular Vision, 17, 86, 756-767 (2011)

[16] S. Hartung, "Image Subtraction Noise Reduction Using Point Spread Function Cross-correlation", arXiv: 1301.1413 [astro-ph.IM], (2013)

[17] Lopez-Gil, N; Artal, P, "Reconstruction of the point-spread function of the human eye from two double-pass retinal images by phase-retrieval algorithms". JOURNAL OF THE OPTICAL SOCIETY OF AMERICA A-OPTICS IMAGE SCIENCE AND VISION. 15, 326-39, (1998-2)

[18] M. G. Kang, K. 1. Lay, A. K. Katsaggelos, "Phase estimation using the bispectrum and its application to image restoration" OPTICAL ENGINEERING, 30 No. 7, (1991)

[19] Wen, Z. Y.; Fraser, D.; Lambert, A.; Li, H. D., "Reconstruction of Underwater Image by Bispectrum," Image Processing, 2007. ICIP 2007 IEEE International Conference on, 3, no., pp. III-545, III-548, (2007)

[20] Loeb, Gerald E., Mark W. White, and Michael M. Merzenich. "Spatial cross-correlation" Biological cybernetics 47.3, 149-163, (1983)

[21] C. F. Hester; and D. Casasent, "Multivariant technique for multiclass pattern recognition." Applied Optics 19.11, 1758-1761, (1980)

[22] W. Lei; M. Anderle; G. W Rubloff, "Real-time sensing and metrology for atomic layer deposition processes and manufacturing", Vacuum Science & Technology, B 25, 130-139 (2007)

[23] S. Cho, L. Henn-Lecordier, Y. Liu, and G. W. Rubloff. "In situ mass spectrometry in a 10 Torr W chemical vapor deposition process for film thickness metrology and real-time advanced process control", Vacuum Science & Technology, B 22, 880 (2004)

[24] T. Tiwald; C. Bungay; A. E. Hooper, "Measuring the thickness of organic/polymer/biological films on glass substrates using spectroscopic ellipsometry", Vacuum Science & Technology, A 24, 1605-1609 (2006)

[25] A. J. Gonzales and E. M. Philofsky, "Applications of scanning electron microscopy to thin film studies on semiconductor devices", Proc. IEEE 59, 1429-1433 (1971).

[26] Bogner A, Jouneau P H, Thollet G, Basset D, Gauthier C. A history of scanning electron microscopy developments: Towards "wet-STEM" imaging. Micron 38, 390-401 (2007)

[27] R. M. A. Azzam and N. M. Bashara, Ellipsometry and Polarized Light (1979)

[28] H. G. Tompkins and W. A. McGahan, Spectroscopic Ellipsometry and Reflectometry: A User's Guide (1999)

[29] S. W. Kim and G. H. Kim, "Thickness-profile measurement of transparent thin-film layers by white-light scanning interferometry," Appl. Opt. 38, 5968-5973 (1999).

[30] P. Groot, and X. C. Lega, "Angle-resolved three-dimensional analysis of surface films by coherence scanning interferometry" Opt. Lett, 32, 1638-1640 (2007)

[31] D. S. Wan, "Measurement of thin films using Fourier amplitude," U.S. Pat. No. 7,612,891 B2 (2009)

[32] Simon, J., "New noncontact devices for measuring small micro displacements", App. Opt. 9(10), p. 2337, (1970)

[33] Wyant, J. C., L. R. Baker and H. E. Bennett, "Optical profilers for surface roughness", Proc. SPIE, 525, p. 174-180, (1985)

[34] Reid, G. T., Rixon, R. C., and Messer, H. I., "Absolute and comparative measurements of three dimensional shape by phase measuring moiré topography", Opt. and Laser Tech. 16, p. 315-319, (1984)

[35] Gabor, D. "A New Microscope Principle", Nature 161, p. 40-98, (1948)

[36] Whitehouse, D. J., "Handbook of surface metrology", IOP Publishing, Ltd., London, (1994)

[37] Bennett, J. M., and Mattsson, L., "Introduction to Surface Roughness and Scattering", Opt. Soc. Of America, Washington, D.C., (1989)

[38] Balasubramanian, N., "Optical system for surface topography measurement", U.S. Pat. No. 4,340,306, (1982)

[39] Gu, M., and Bird, D, "Fibre-optic double-pass confocal microscopy", Optics & Laser Technol. 30, p. 91-93, (1998)

It will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software can include instructions executable by a processor that, in response to such execution, cause a processor or any other circuitry to perform a set of operations, steps, methods, processes, algorithms, etc.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A measurement method comprising:
   illuminating an object to be measured with light at two different known wavelengths and a known incident angle;
   capturing an image of the object using a camera;
   applying one or more of Fractional Bi-Spectrum Analysis and Fractional Cross Correlation to two different frequency components of the image corresponding to the two different known wavelengths; and
   mitigating signal noise resulting in a speckle pattern associated with the image and calculating a thickness of the object based on the one or more of the Fractional Bi-Spectrum Analysis and the Fractional Cross Correlation.

2. The measurement method of claim 1, wherein the thickness is calculated based on a relationship between the thickness and the frequency of the interference pattern.

3. A measurement system comprising:
   one or more light sources illuminating an object to be measured with light at two different known wavelengths and a known incident angle;
   a camera capturing an image of the object; and
   a computer applying one or more of Fractional Bi-Spectrum Analysis and Fractional Cross Correlation to two different frequency components of the image corresponding to the two different known wavelengths, and mitigating signal noise resulting in a speckle pattern associated with the image and calculating a thickness of the object based on the one or more of the Fractional Bi-Spectrum Analysis and the Fractional Cross Correlation.

4. The measurement system of claim 3, wherein the thickness is calculated based on a relationship between the thickness and the frequency of the interference pattern.

\* \* \* \* \*